(12) United States Patent
Ho et al.

(10) Patent No.: US 10,723,841 B2
(45) Date of Patent: Jul. 28, 2020

(54) METHOD FOR PREPARING COMPOUND AND METHOD FOR PREPARING POLYMER EMPLOYING THE SAME

(71) Applicant: INDUSTRIAL TECHNOLOGY RESEARCH INSTITUTE, Hsinchu (TW)

(72) Inventors: Po-Hsien Ho, Taipei (TW); Chih-Hsiang Lin, Taipei (TW); Feng-Jen Tsai, Taipei (TW); Cheng-Hsing Fan, Tainan (TW); Yih-Her Chang, Baoshan Township (TW); Hsin-Ching Kao, Baoshan Township (TW); Chien-Ming Chen, Taoyuan (TW)

(73) Assignee: INDUSTRIAL TECHNOLOGY RESEARCH, Hsinchu (TW)

( * ) Notice: Subject to any disclaimer, the term of this patent is extended or adjusted under 35 U.S.C. 154(b) by 41 days.

(21) Appl. No.: 16/047,674

(22) Filed: Jul. 27, 2018

(65) Prior Publication Data

US 2019/0040202 A1 Feb. 7, 2019

Related U.S. Application Data

(60) Provisional application No. 62/539,681, filed on Aug. 1, 2017.

(30) Foreign Application Priority Data

Dec. 27, 2017 (TW) .............................. 106145978 A

(51) Int. Cl.
*C08G 75/0236* (2016.01)
*C07C 319/14* (2006.01)
(Continued)

(52) U.S. Cl.
CPC ........ *C08G 75/0236* (2013.01); *C07C 315/00* (2013.01); *C07C 315/02* (2013.01); *C07C 317/22* (2013.01); *C07C 319/14* (2013.01); *C07C 319/20* (2013.01); *C07C 323/00* (2013.01); *C08G 75/02* (2013.01);
(Continued)

(58) Field of Classification Search
CPC .... C07F 7/0801; C07F 7/0832; C07F 7/0827; C08G 75/00; C07B 51/00; C07D 209/12
See application file for complete search history.

(56) References Cited

U.S. PATENT DOCUMENTS 3,634,355 A 1/1972 Barr et al.
8,143,453 B2 3/2012 Reddy et al.
(Continued)

FOREIGN PATENT DOCUMENTS

CN 101033294 A 9/2007
CN 101092479 A 12/2007
(Continued)

OTHER PUBLICATIONS

Dizman, C., et al, "Recent advances in the preparation of functionalized polysulfones," Polymer International, 2013, vol. 62, p. 991-1007.
(Continued)

*Primary Examiner* — Shane Fang
(74) *Attorney, Agent, or Firm* — Birch, Stewart, Kolasch & Birch, LLP

(57) ABSTRACT

A method for preparing a compound and a method for preparing a polymer employing the same are provided. The method for preparing a compound includes reacting a compound having a structure represented by Formula (I) with a compound having a structure represented by Formula (III) in the presence of a compound having a structure represented by Formula (II) to obtain a compound having a structure represented by Formula (IV)

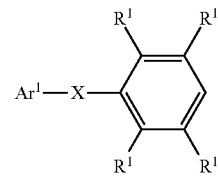

Formula (I)

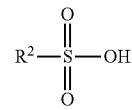

Formula (II)

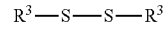

Formula (III)

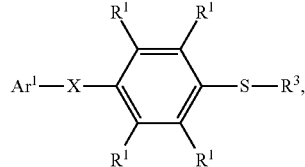

Formula (IV)

wherein $Ar^1$ is substituted or unsubstituted aryl group; X is —O—, —S—, or —NH—; $R^1$ is independently hydrogen or $C_{1-6}$ alkyl group; $R^2$ is hydroxyl group, $C_{1-6}$ alkyl group, phenyl group, or tolyl group; and $R^3$ is independently $C_{1-6}$ alkyl group, $C_{5-8}$ cycloalkyl group, or $C_{2-6}$ alkoxyalkyl group.

27 Claims, No Drawings

(51) Int. Cl.

| | |
|---|---|
| *C07C 315/02* | (2006.01) |
| *C08G 75/0227* | (2016.01) |
| *C08G 75/029* | (2016.01) |
| *C08G 75/23* | (2006.01) |
| *C08G 75/02* | (2016.01) |
| *C07C 319/20* | (2006.01) |
| *C07C 317/22* | (2006.01) |
| *C07C 323/00* | (2006.01) |
| *C08G 75/20* | (2016.01) |
| *C08G 75/025* | (2016.01) |
| *C07C 315/00* | (2006.01) |

(52) U.S. Cl.
CPC ......... *C08G 75/025* (2013.01); *C08G 75/029* (2013.01); *C08G 75/0227* (2013.01); *C08G 75/0272* (2013.01); *C08G 75/20* (2013.01); *C08G 75/23* (2013.01)

(56) References Cited

U.S. PATENT DOCUMENTS

| | | |
|---|---|---|
| 9,045,598 B2 | 6/2015 | El-Toufaili et al. |
| 2003/0004302 A1 | 1/2003 | Okamoto et al. |
| 2015/0065677 A1 | 3/2015 | El-Toufaili et al. |

FOREIGN PATENT DOCUMENTS

| | | |
|---|---|---|
| CN | 101774953 A | 7/2010 |
| CN | 102516139 A | 6/2012 |
| CN | 105492498 A | 4/2016 |
| EP | 3190139 A1 | 7/2017 |
| EP | 3190140 A1 | 7/2017 |
| EP | 3190141 A1 | 7/2017 |
| EP | 3190142 A1 | 7/2017 |
| EP | 3190143 A1 | 7/2017 |
| JP | 7-304872 A | 11/1995 |
| JP | 8-245558 A | 9/1996 |
| JP | 2016-147955 A | 8/2016 |
| JP | 2017-125014 A | 7/2017 |
| JP | 2017-125190 A | 7/2017 |
| JP | 2017-160185 A | 9/2017 |
| JP | 2017-197712 A | 11/2017 |
| JP | 2017-197713 A | 11/2017 |
| TW | 201512249 A | 4/2015 |

OTHER PUBLICATIONS

Matsumoto, K., et al, "Synthesis of poly(ether sulfone)s by self-polycondensation of AB-type monomers," Polymer Journal, 2013, vol. 45, pp. 909-914.

Tsuchida, E., et al, "Synthesis of High Molecular Weight Poly(phenylene sulfide) by Oxidative Polymerization via Poly(sulfonium cation) from Methyl Phenyl Sulfoxide," Macromolecules, 1993, vol. 26, pp. 7144-7148.

Tsuchida, E., et al, "Synthetic Route to Poly(sulfonyl-1,4-phenylenethio-1,4-phenylene) via a Poly(sulfonium cation)," Macromolecules, 1993. vol. 26, pp. 7389-7390.

Yokozawa, T., et al, "Chain-growth polycondensation: The living polymerization process in polycondensation," Progress in Polymer Science, Jan. 1, 2007, vol. 32, pp. 147-172.

Taiwanese Notice of Allowance and Search Report, dated Dec. 25, 2018, for Taiwanese Application No. 106145978.

Cogolli et al., "Nucleophilic Aromatic Substitution Reactions of Unactivated Aryl Halides With Thiolate Ions in Hexamethylphosphoramide", The Journal of Organic Chemistry, vol. 44, No. 15, Jul. 1, 1979, pp. 2642-2646.

Ding et al., "Preparation of Poly(thioarylene)s From Cyclic Disulfide Oligomers", Macromolecules, American Chemical Society, vol. 30, No. 9, May 5, 1997 (abstract published Apr. 1997), pp. 2527-2531.

Extended European Search Report dated Jan. 4, 2019, for corresponding European Application No. 18186311.9.

Gabler et al., "Neue Polyphenylensulfone Reaktionen An Festen Polymeren", Chimia International Journal for Chemistry, vol. 28, No. 9. Sep. 1974, pp. 567-575.

Miller et al., "Reactions of Diaryl Disulfides with Active, Non-nucleophilic Alkylating Agents", Journal of Organic Chemistry, vol. 36, No. 11, Jun. 1, 1971, pp. 1513-1519.

Tsuchida et al., "Polymerization at Diphenyl Disulfide by the S—S Bond Cleavage With a Lewis Acid: A Novel Preparation Route to Poly(p-phenylene sulfide)", Macromolecules, vol. 23, No. 8, Apr. 16, 1990 pp. 2101-2106.

Japanese Office Action dated Jun. 25, 2019, for corresponding Japanese Application No. 2018-142980, with English translation.

Jílek et al., "Potential metabolites of the neuroleptic agents belonging to the 8-(methylthio)-10-piperazino-10,11-dihydrodibenzo[b,f]thiepin series; Synthesis of 2-hydroxy and 3-hydroxy derivatives", Collection Czechoslovak Chem. Commun., vol. 50, 1985, pp. 2179-2190.

METHOD FOR PREPARING COMPOUND AND METHOD FOR PREPARING POLYMER EMPLOYING THE SAME

CROSS REFERENCE TO RELATED APPLICATIONS

This application claims the benefit of U.S. Provisional Application No. 62/539,681, filed on Aug. 1, 2017, which is hereby incorporated by reference herein.

The application is based on, and claims priority from, Taiwan Application Serial Number 106145978, filed on Dec. 27, 2017, the disclosure of which is hereby incorporated by reference herein in its entirety.

TECHNICAL FIELD

The technical field relates to a method for preparing a compound and a method for preparing a polymer.

BACKGROUND

Polyarylene sulfide (PAS) (or polythioether sulfone (PTES)) is a material with good physical characteristics such as thermal resistance, chemical resistance, flame resistance, non-toxicity, and electrical insulation characteristics. Thus, polyarylene sulfide (PAS) (or polythioether sulfone (PTES)) can be used in computer accessories and auto accessories; as a coating for parts that come into contact with corrosive chemicals; and as industrial fibers having chemical resistance.

However, conventional methods for preparing polyarylene sulfide (PAS), polythioether sulfone (PTES), or monomers thereof are halogen-containing processes that, in principle, results in a low yield and produces unrecyclable halogen-containing byproducts that can cause environmental pollution.

SUMMARY

According to embodiments of the disclosure, the disclosure provides a method for preparing a compound. The method includes the following steps. A compound having a structure represented by Formula (I) is reacted with a compound having a structure represented by Formula (III) in the presence of a compound having a structure represented by Formula (II), obtaining a compound having a structure represented by Formula (IV)

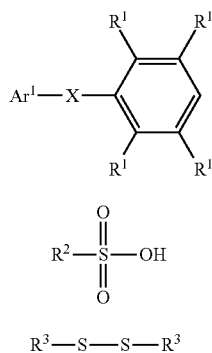
Formula (I)

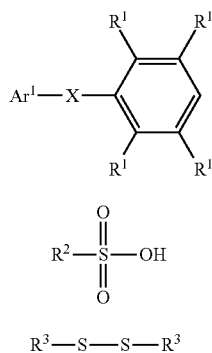
Formula (II)

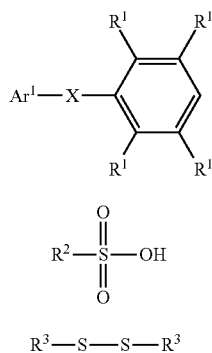
Formula (III)

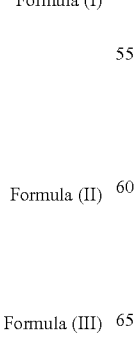
Formula (IV)

wherein $Ar^1$ is substituted or unsubstituted aryl group; X is —O—, —S—, or —NH—; $R^1$ is independently hydrogen or $C_{1-6}$ alkyl group; $R^2$ is hydroxyl group, $C_{1-6}$ alkyl group, phenyl group, or tolyl group; and $R^3$ is independently $C_{1-6}$ alkyl group, $C_{5-8}$ cycloalkyl group, or $C_{2-6}$ alkoxyalkyl group.

According to embodiments of the disclosure, the disclosure also provides a method for preparing a polymer. The method includes the following steps. A compound having a structure represented by Formula (I) is reacted with a compound having a structure represented by Formula (III) in the presence of a compound having a structure represented by Formula (II), obtaining a compound having a structure represented by Formula (IV). The compound having the structure represented by Formula (IV) is reacted with a compound (A), obtaining a compound having the structure represented by Formula (V). The compound (A) is nitric acid, sulfuric acid, acetic acid, hydrogen peroxide, or a combination thereof. The compound having the structure represented by Formula (V) is reacted with a compound having a structure represented by Formula (VI), obtaining a polymer having a repeat unit represented by Formula (VII)

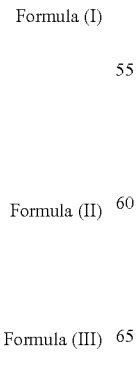
Formula (I)

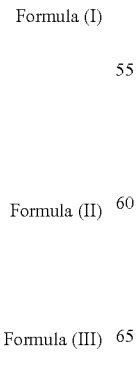
Formula (II)

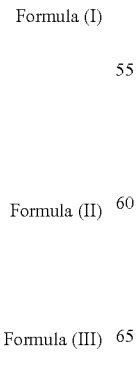
Formula (III)

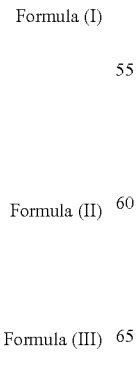
Formula (IV)

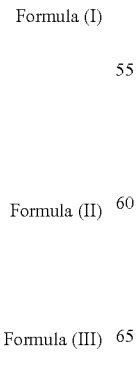
Formula (V)

-continued

Formula (VI)

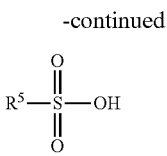

Formula (VII)

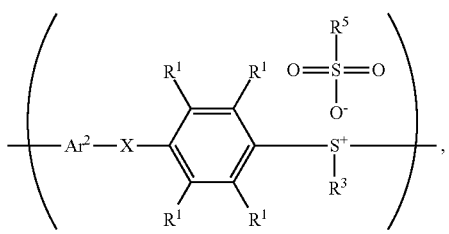

wherein $Ar^1$ is substituted or unsubstituted aryl group; X is —O—, —S—, or —NH—; $R^1$ is independently hydrogen or $C_{1-6}$ alkyl group; $R^2$ is hydroxyl group, $C_{1-6}$ alkyl group, phenyl group, or tolyl group; $R^3$ is independently $C_{1-6}$ alkyl group, $C_{5-8}$ cycloalkyl group, or $C_{2-6}$ alkoxyalkyl group; $R^5$ is hydroxyl group, $C_{1-6}$ alkyl group, phenyl group, or tolyl group; and $Ar^2$ is substituted or unsubstituted aryl diradical.

A detailed description is given in the following embodiments with reference to the accompanying drawings.

DETAILED DESCRIPTION

The disclosure provides a method for preparing a compound, wherein the starting materials or catalysts of the method for preparing a compound are halogen-free compounds. Thus, no halogen-containing side product is formed. In addition, there is no halogen-containing compound remained in the obtained result. The method for preparing a compound of the disclosure does not include an additional step for removing a halogen-containing side product or residual halogen-containing compound, thereby reducing preparation cost and increasing product yield. Thus, a halogen-free monomer, which can be used in a subsequent polymerization, is obtained.

Furthermore, the disclosure also provides a method for preparing a polymer (such as polyether sulfone (PES) or polythioether sulfone (PTES). The starting materials of the method for preparing the monomer of the polymer and the method for preparing a polymer are halogen-free compounds. Thus, no halogen-containing side product is formed. In addition, there is no halogen-containing compound remained in the obtained result. The method for preparing a polymer of the disclosure does not include an additional step for removing a halogen-containing side product or residual halogen-containing compound, thereby reducing preparation cost and increasing product yield. Thus, a halogen-free polymer is obtained. Furthermore, the method for preparing a polymer of the disclosure includes subjecting a monomer to an electrophilic polymerization and then performing an oxidation after polymerization. Therefore, the obtained polymer has an increased molecular weight and a reduced polydispersity index (PDI).

According to embodiments of the disclosure, the disclosure provides a method for preparing a compound, wherein the compound can serve as a monomer for a subsequent polymerization (such as polyether sulfone (PES) polymerization or polythioether sulfone (PTES) polymerization). The method for preparing a compound includes: reacting a compound having a structure represented by Formula (I) with a compound having a structure represented by Formula (III) in the presence of a compound having a structure represented by Formula (II), obtaining a compound having a structure represented by Formula (IV)

Formula (I)

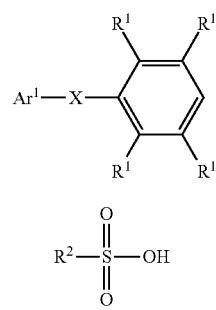

Formula (II)

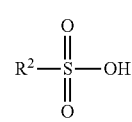

Formula (III)

Formula (IV)

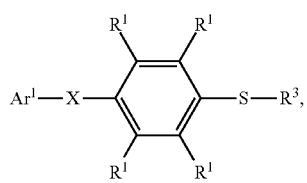

wherein $Ar^1$ can be substituted or unsubstituted aryl group; X can be —O—, —S—, or —NH—; $R^1$ can be independently hydrogen or $C_{1-6}$ alkyl group; $R^2$ can be hydroxyl group, $C_{1-6}$ alkyl group, phenyl group, or tolyl group; and $R^3$ can be independently $C_{1-6}$ alkyl group, $C_{5-8}$ cycloalkyl group, or $C_{2-6}$ alkoxyalkyl group. Herein, the substituted aryl group of the disclosure means that at least one hydrogen atom bonded to carbon atoms of the aryl group can be replaced with $C_{1-6}$ alkyl group.

According to embodiments of the disclosure, wherein $Ar^1$ can be substituted or unsubstituted phenyl group, biphenyl group, naphthyl group, thienyl group, indolyl group, phenanthrenyl group, indenyl group, anthracenyl group, or fluorenylene group. In particular, the substituted phenyl group, substituted biphenyl group, substituted naphthyl group, substituted thienyl group, substituted indolyl group, substituted phenanthrenyl group, substituted indenyl group, substituted anthracenyl group, or substituted fluorenylene group means that at least one hydrogen atom bonded to carbon atoms of the aforementioned group can be replaced with $C_{1-6}$ alkyl group.

According to embodiments of the disclosure, $C_{1-6}$ alkyl group can be linear or branched alkyl group, such as methyl group, ethyl group, propyl group, isopropyl group, n-butyl group, t-butyl group, sec-butyl group, isobutyl group, pentyl group, or hexyl group.

According to embodiments of the disclosure, $R^1$ can be independently hydrogen, methyl group, ethyl group, propyl group, isopropyl group, n-butyl group, t-butyl group, sec-butyl group, isobutyl group, pentyl group, or hexyl group.

According to embodiments of the disclosure, $R^2$ can be hydroxyl group, methyl group, ethyl group, propyl group, isopropyl group, n-butyl group, t-butyl group, sec-butyl group, isobutyl group, pentyl group, hexyl group, phenyl group, or tolyl group.

According to embodiments of the disclosure, $R^3$ can be independently methyl group, ethyl group, propyl group, isopropyl group, n-butyl group, t-butyl group, sec-butyl group, isobutyl group, pentyl group, hexyl group, cyclopentyl group, cyclohexyl group, cycloheptyl group, cyclooctyl group, or

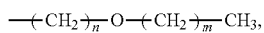

wherein $1 \leq n \leq 5$, $0 \leq m \leq 4$, and $1 \leq n+m \leq 5$.

According to embodiments of the disclosure, The compound having the structure of Formula (I) can be

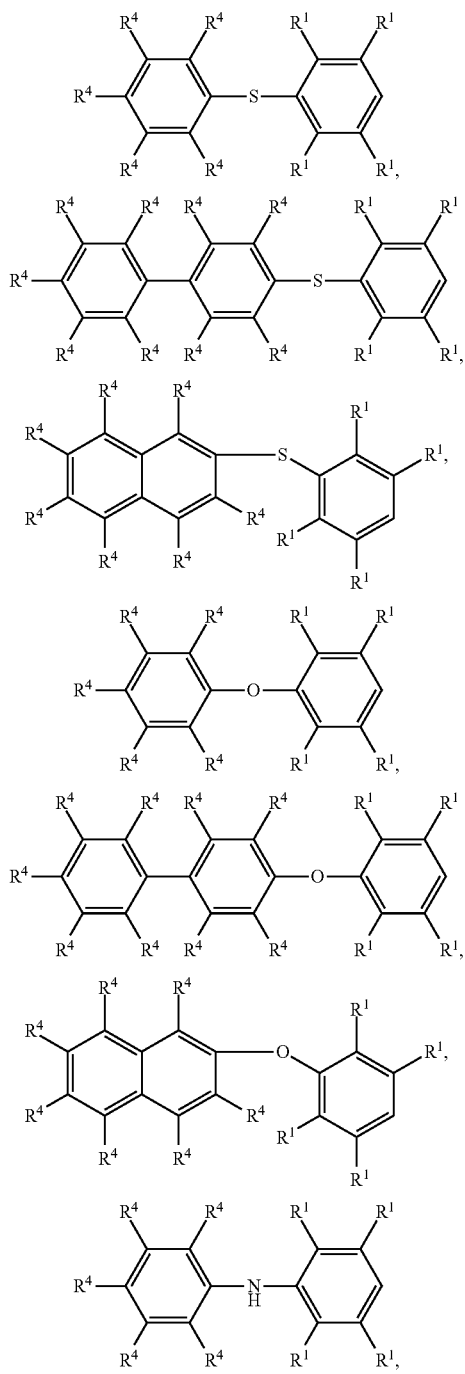

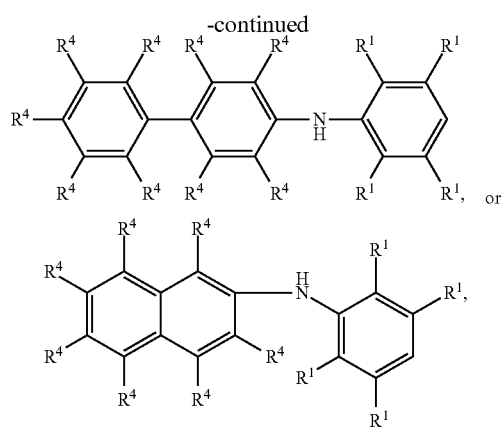

wherein $R^1$ has the same definition as above; and $R^4$ can be independently hydrogen or $C_{1-6}$ alkyl group.

According to embodiments of the disclosure, $R^4$ can be independently hydrogen, methyl group, ethyl group, propyl group, isopropyl group, n-butyl group, t-butyl group, sec-butyl group, isobutyl group, pentyl group, or hexyl group.

According to embodiments of the disclosure, the compound having the structure of Formula (II) can be sulfuric acid, methanesulfonic acid, benzenesulfonic acid, p-toluenesulfonic acid, or a combination thereof.

According to embodiments of the disclosure, the compound having the structure of Formula (III) can be

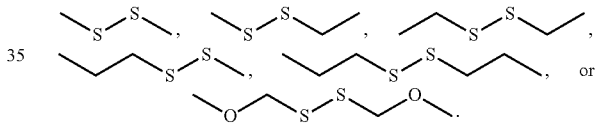

According to embodiments of the disclosure, the disclosure provides a method for preparing the compound having the structure of Formula (IV), wherein the compound having the structure of Formula (IV) can be

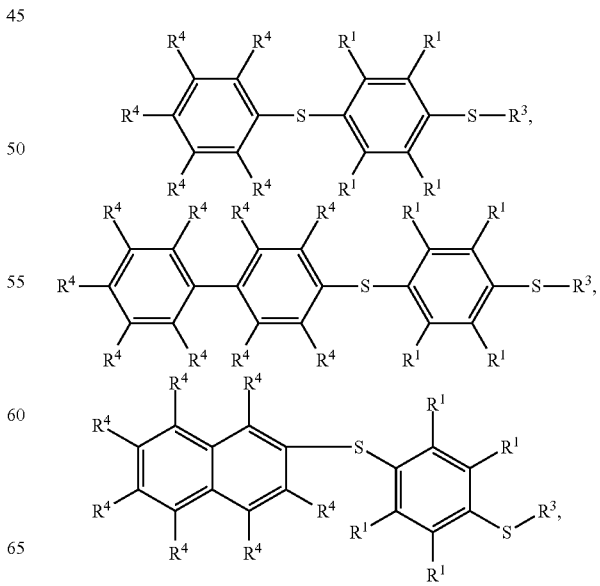

-continued

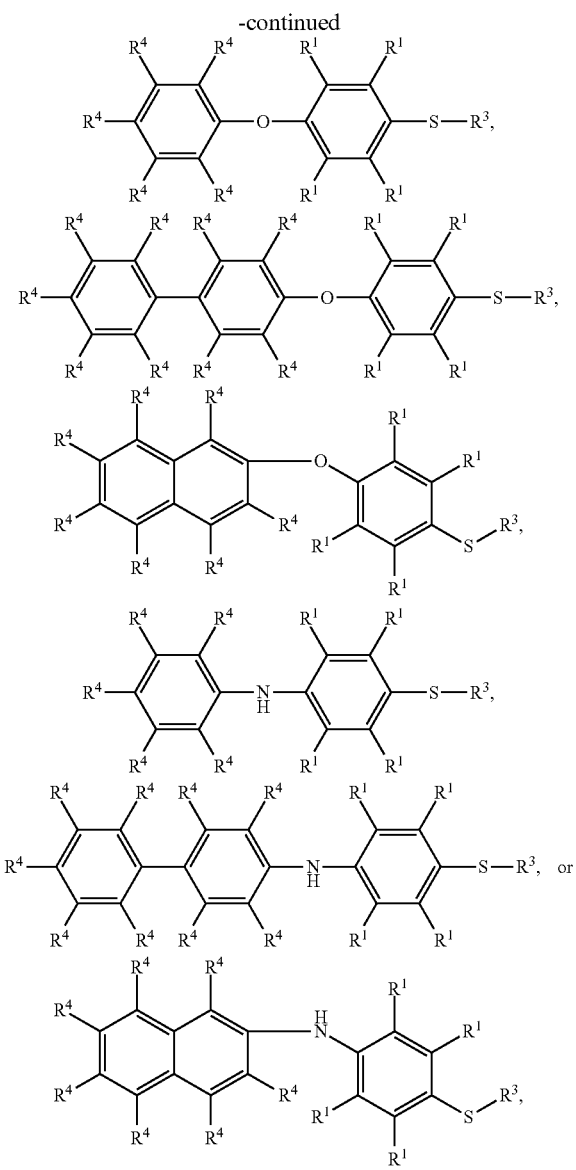

wherein $R^1$, $R^3$, and $R^4$ have the same definition as above.

According to embodiments of the disclosure, the method for preparing the compound having the structure of Formula (IV) of the disclosure can include dissolving the compound having the structure of Formula (I) and the compound having the structure of Formula (II) in a solvent, obtaining a mixture. Next, the compound having the structure of Formula (III) is added into the mixture to undergo a reaction, obtaining a compound having a structure represented by Formula (IV). The synthesis pathway of the above reaction is as follows:

-continued wherein $Ar^1$, X, $R^1$, $R^2$, and $R^3$ have the same definition as above. Herein, the solvent can be any solvent (such as halogen-free organic solvent) which can be used to dissolve the compound having the structure of Formula (I) and the compound having the structure of Formula (II). Furthermore, a halogen-containing organic solvent, which is easily removed after the reaction is complete and would not be active in the desired reaction, can also serve as the solvent of the above reaction. According to embodiments of the disclosure, the solvent can be an aprotic solvent. The solvent, for example, can include acetonitrile, linear or cyclic alkane (such as propane, butane, or cyclohexane), haloalkane (dichloromethane, trichloromethane, or dichloroethane). Furthermore, the reaction can be performed in the absence of a solvent.

According to embodiments of the disclosure, in the method for preparing the compound of the disclosure, the molar ratio of the compound having the structure of Formula (II) to the compound having the structure of Formula (I) can be from about 0.5 to 5; Furthermore, in the method for preparing the compound of the disclosure, The molar ratio of the compound having the structure of Formula (I) to the compound having the structure of Formula (III) can be from about 1 to 20, such as from about 1 to 3, or from about 1 to 10.

According to some embodiments of the disclosure, the method for preparing the compound of the disclosure, after preparing the compound having the structure of Formula (IV), further includes reacting the compound having the structure represented by Formula (IV) with a compound (A), obtaining a compound having the structure represented by Formula (V)

Formula (V)

wherein the compound (A) can be nitric acid, sulfuric acid, acetic acid, hydrogen peroxide, or a combination thereof; and $Ar^1$, X, and $R^3$ has the same definition as above.

According to embodiments of the disclosure, the disclosure provides a method for preparing the compound having the structure of Formula (V), wherein the compound having the structure of Formula (V) can be

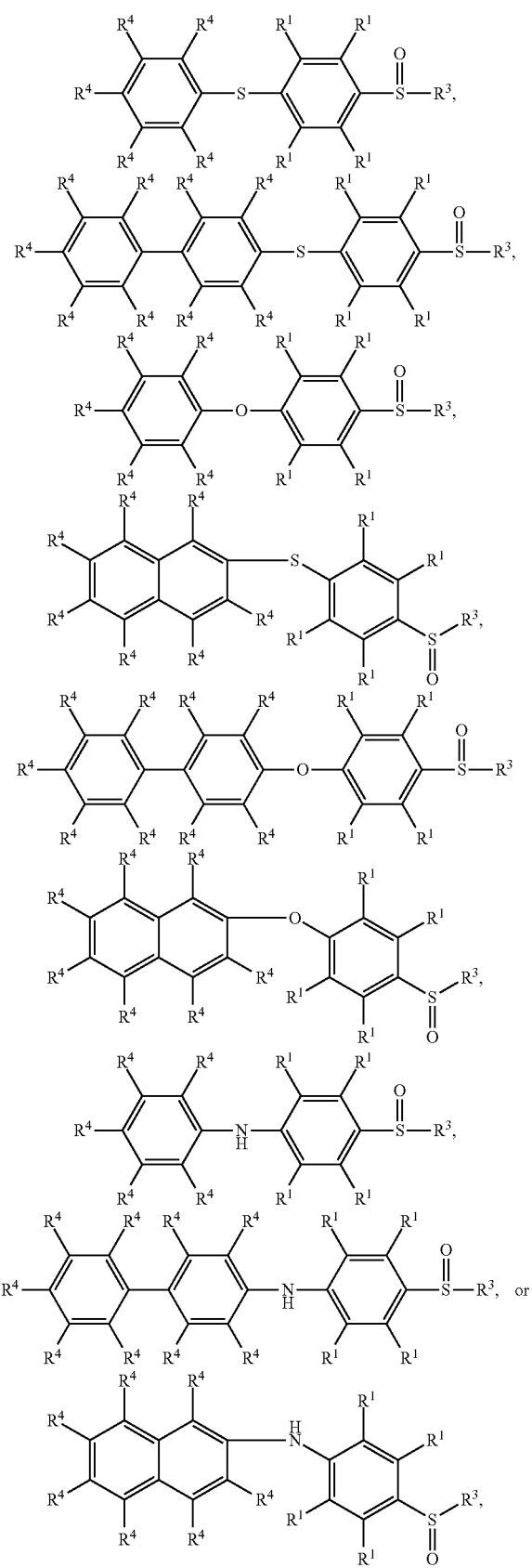

wherein $R^1$, $R^3$, and $R^4$ have the same definition as above.

According to embodiments of the disclosure, the method for preparing the compound having the structure of Formula (V) of the disclosure can include dissolving the compound having the structure of Formula (I) and the compound having the structure of Formula (II) in a first solvent, obtaining a mixture. Next, the compound having the structure of Formula (III) is added into the mixture to undergo a reaction, obtaining a compound having a structure represented by Formula (IV). Next, the compound having the structure of Formula (IV) is dissolved in a second solvent, and the compound (A) is added to undergo a reaction, obtaining a compound having the structure represented by Formula (V). The synthesis pathway of the above reaction is as follows:

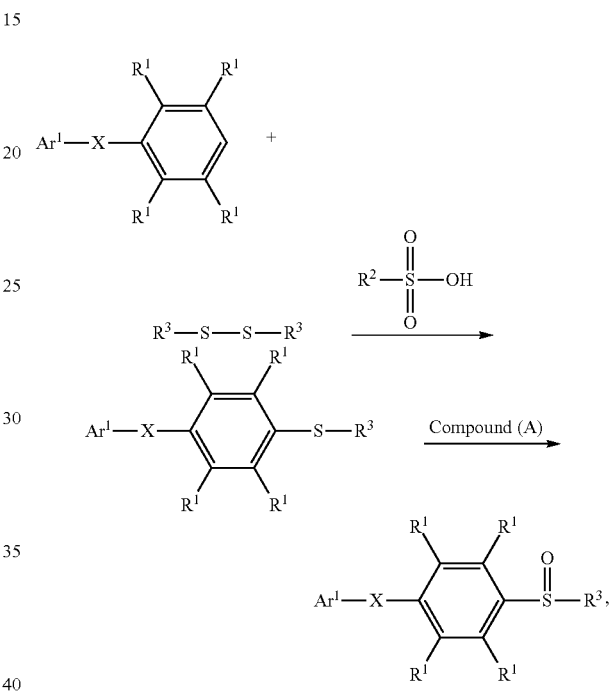

wherein $Ar^1$, X, $R^1$, $R^2$ and $R^3$ have the same definition as above. Herein, when X is S, the S atom bonded to $R^3$ group can be selectively oxidized in comparison with X since the S atom bonded to $R^3$ group exhibits a relatively low steric hindrance and has a suitable oxidation potential for oxidation.

According to embodiments of the disclosure, the first solvent can be any solvent which can be used to dissolve the compound having the structure of Formula (I) and the compound having the structure of Formula (II). The second solvent can be any solvent which can be used to dissolve the compound having the structure of Formula (IV). According to embodiments of the disclosure, a halogen-free organic solvent can serve as the first solvent or the second solvent. Furthermore, a halogen-containing organic solvent, which is easily removed after the reaction is complete and would not be active in the desired reaction, can also serve as the solvent of the above reaction. According to embodiments of the disclosure, the first solvent or the second solvent can be an aprotic solvent. The solvent, for example, can include acetonitrile, linear or cyclic alkane (such as propane, butane, or cyclohexane), or haloalkane (dichloromethane, trichloromethane, or dichloroethane). Furthermore, the reaction can be performed in the absence of a solvent. The molar ratio of the compound having the structure of Formula (IV) to the compound (A) can be from about 0.8 to 30.

According to embodiments of the disclosure, the disclosure provides a method for preparing a polymer. The method for preparing a polymer includes the following steps. First, a compound having a structure represented by Formula (I) is reacted with a compound having a structure represented by Formula (III) in the presence of a compound having a structure represented by Formula (II), obtaining a compound having a structure represented by Formula (IV). Next, the compound having the structure represented by Formula (IV) is reacted with a compound (A), obtaining a compound having the structure represented by Formula (V), wherein the compound (A) is nitric acid, sulfuric acid, acetic acid, hydrogen peroxide, or a combination thereof. Next, the compound having the structure represented by Formula (V) is reacted with a compound having a structure represented by Formula (VI), obtaining a polymer having a repeat unit represented by Formula (VII)

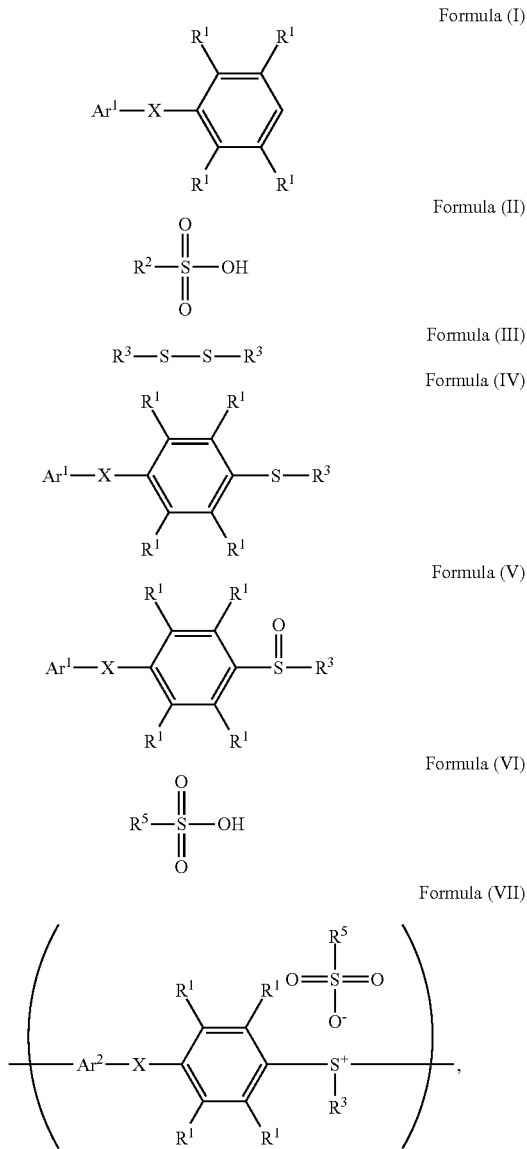

wherein $Ar^1$, X, $R^1$, $R^2$, and $R^3$ has the same definition as above; $R^5$ is hydroxyl group, $C_{1-6}$ alkyl group, phenyl group, or tolyl group; and $Ar^2$ is substituted or unsubstituted aryl diradical. The method for preparing a polymer of the disclosure can be used to prepare a polymer having a number average molecular weight greater than or equal to 1,000. It should be noted that the method for preparing a polymer of the disclosure is particularly suitable for preparing a polymer having a great number average molecular weight (such as greater than or equal to 80,000) and a narrow polydispersity index (PDI) (such as less than or equal to 2). According to embodiments of the disclosure, the method for preparing a polymer of the disclosure is particularly suitable for preparing a polymer having a number average molecular weight from 80,000 to 500,000 and a polydispersity index (PDI) from 1 to 2. According to some embodiments of the disclosure, the method for preparing a polymer of the disclosure is particularly suitable for preparing a polymer having a number average molecular weight from 80,000 to 200,000 and polydispersity index (PDI) from 1.4 to 2.

According to embodiments of the disclosure, $R^5$ can be hydroxyl, methyl group, ethyl group, propyl group, isopropyl group, n-butyl group, t-butyl group, sec-butyl group, isobutyl group, pentyl group, hexyl group, phenyl group, or tolyl group.

According to embodiments of the disclosure, the substituted aryl diradical of the disclosure means that at least one hydrogen atom bonded to carbon atoms of the aryl diradical can be replaced with $C_{1-6}$ alkyl group.

According to embodiments of the disclosure, $Ar^2$ can be substituted or unsubstituted phenylene group, biphenylene group, naphthylene group, thienylene group, indolylene group, phenanthrenylene group, indenylene group, anthracenylene group, or fluorenylene group. In particular, the substituted phenylene group, substituted biphenylene group, substituted naphthylene group, substituted thienylene group, substituted indolylene group, substituted phenanthrenylene group, substituted indenylene group, substituted anthracenylene group, or substituted fluorenylene group means that at least one hydrogen atom bonded to carbon atoms of the aforementioned group can be replaced with $C_{1-6}$ alkyl group.

According to embodiments of the disclosure, in the method for preparing the polymer of the disclosure, the molar ratio of the compound having the structure of Formula (II) to the compound having the structure of Formula (I) can be from about 0.5 to 5. Furthermore, in the method for preparing the compound of the disclosure, the molar ratio of the compound having the structure of Formula (I) to the compound having the structure of Formula (III) can be from about 1 to 20, such as from about 1 to 3, or from about 1 to 10. The molar ratio of the compound having the structure of Formula (IV) to the compound (A) (such as nitric acid, sulfuric acid, acetic acid, hydrogen peroxide, or a combination thereof) can be from about 0.8 to 30; and the molar ratio of the compound having the structure of Formula (V) to the compound having the structure of Formula (VI) can be from about 0.8 to 20, such as from about 1.2 to 5. Furthermore, the compound having the structure of Formula (VI) can serve as a reactant for reacting with the compound having the structure of Formula (V), and the excessive compound having the structure of Formula (VI) can also serve as the reaction solvent.

According to embodiments of the disclosure, the compound having the structure of Formula (VI) can be sulfuric acid, methanesulfonic acid, benzenesulfonic acid, p-toluenesulfonic acid, trifluoromethanesulfonic acid or a combination thereof. Furthermore, according to embodiments of the disclosure, the compound having the structure of Formula (II) and the compound having the structure of Formula (VI) can be the same or different.

According to embodiments of the disclosure, the method for preparing the polymer of the disclosure can be used to prepare the polymer having a repeat unit represented by Formula (VII). For example, the repeat unit represented by Formula (VII) can be

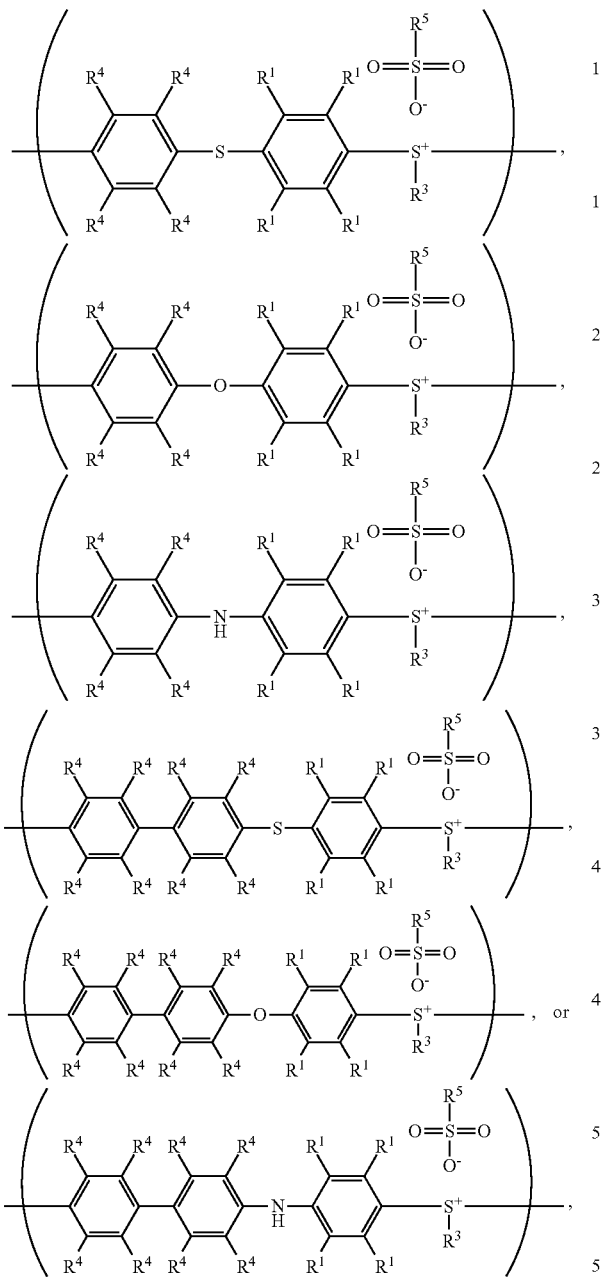

wherein $R^1$, $R^3$, $R^4$, and $R^5$ have the same definition as above.

According to embodiments of the disclosure, the method for preparing the polymer having a repeat unit represented by Formula (VII) of the disclosure can include dissolving the compound having the structure of Formula (I) and the compound having the structure of Formula (II) in a first solvent, obtaining a mixture. Next, the compound having the structure of Formula (III) is added into the mixture to undergo a reaction, obtaining a compound having a structure represented by Formula (IV). Next, the compound having the structure of Formula (IV) is dissolved in a second solvent, the compound (A) is added to undergo a reaction, obtaining a compound having the structure represented by Formula (V). Next, the compound having the structure represented by Formula (V) is reacted with a compound having a structure represented by Formula (VI), obtaining a polymer having a repeat unit represented by Formula (VII). The synthesis pathway for preparing the above polymer is as follows:

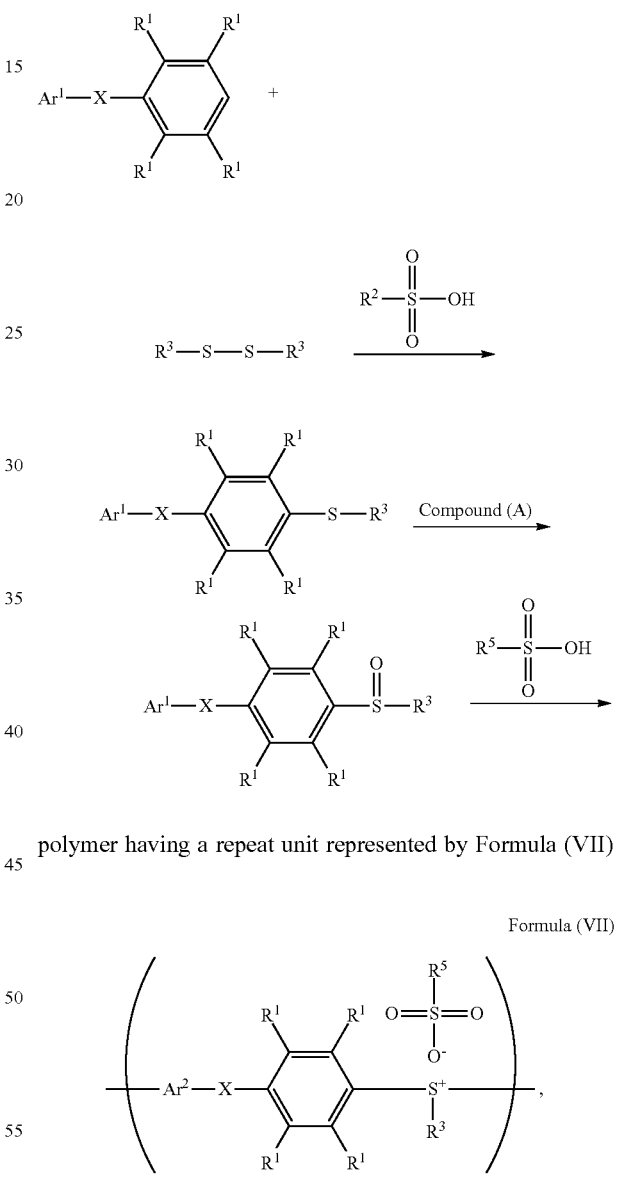

polymer having a repeat unit represented by Formula (VII)

Formula (VII)

wherein $Ar^1$, $Ar^2$, X, $R^1$, $R^2$, $R^3$, and $R^5$ have the same definition as above.

According to embodiments of the disclosure, after preparing the polymer having the repeat unit represented by Formula (VII), the method for preparing the polymer of the disclosure further includes reacting a nucleophile with the polymer having the repeat unit represented by Formula (VII), obtaining a polymer having a repeat unit represented by Formula (VIII)

Formula (VII)

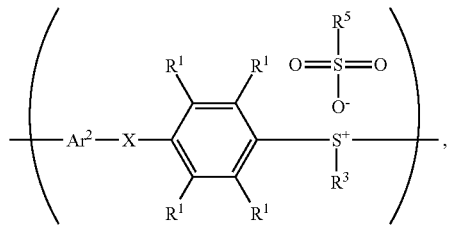

Formula (VIII)

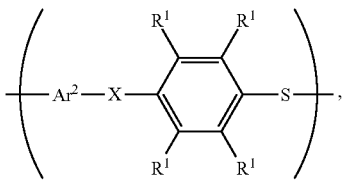

wherein Ar², X, R¹, R³, and R⁵ have the same definition as above. The synthesis pathway of the above method for preparing the polymer having the repeat unit represented by Formula (VIII) is as follows:

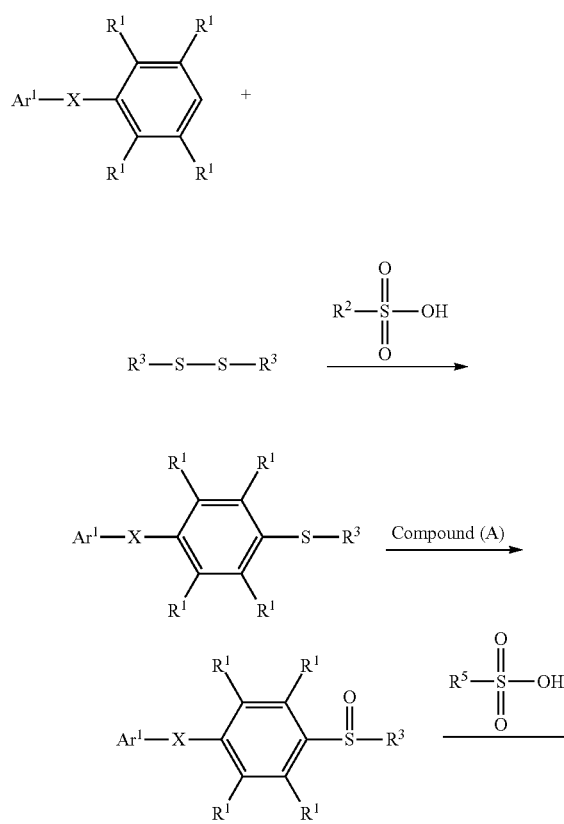

polymer having a repeat unit represented by Formula (VIII)

Formula (VII)

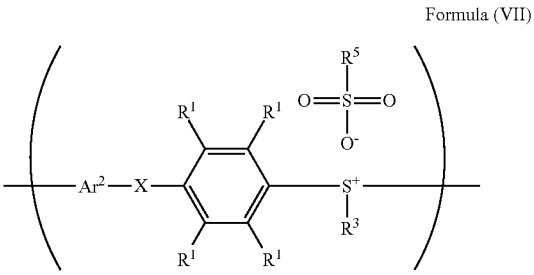

Formula (VIII)

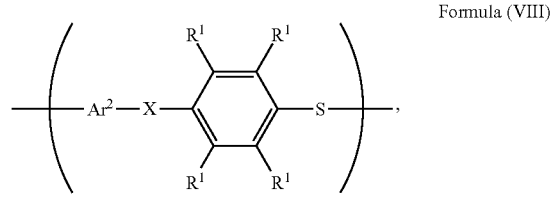

wherein Ar¹, Ar², X, R¹, R², R³ and R⁵ have the same definition as above.

According to embodiments of the disclosure, the nucleophile can be substituted or unsubstituted pyridine or derivatives thereof (such as pyridine or 4-methylpyridine), amine (such as triethylamine), halogenated salt (such as potassium chloride), alcohol (such as methanol or ethanol), amide (such as dimethylformamide, dimethylacetamide, or N-methylpyrrolidone), or a combination thereof. The equivalent ratio of the nucleophile to the moiety represented by

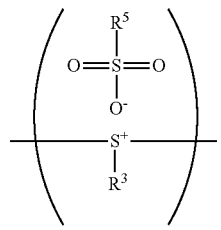

of the polymer having the repeat unit represented by Formula (VII) can be from 1 to 10. According to embodiments of the disclosure, the nucleophile and the polymer having the repeat unit represented by Formula (VII) can optionally be dissolved into an organic solvent before undergoing the reaction.

According to embodiments of the disclosure, when X of the repeat unit represented by Formula (VIII) is —O— or —NH— (i.e. the repeat unit represented by Formula (VIII) is

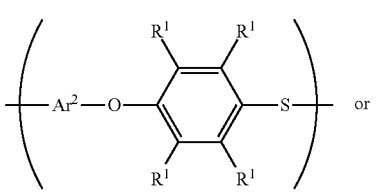 or

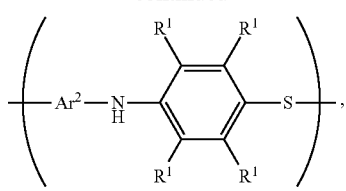

wherein Ar², and R¹ have the same definition as above), the method for preparing the polymer of the disclosure can further include, after obtaining the polymer having the repeat unit represented by Formula (VIII), reacting the polymer having the repeat unit represented by Formula (VIII) with hydrogen peroxide (H₂O₂), obtaining a polymer having a repeat unit represented by Formula (X). Alternatively, the polymer having the repeat unit represented by Formula (VIII) can be reacted with hydrogen peroxide in the presence of the compound having a structure represented by Formula (IX), obtaining the polymer having the repeat unit represented by Formula (X)

Formula (VIII)

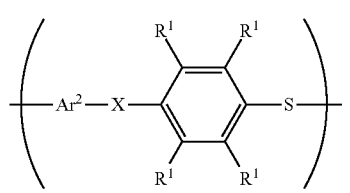

Formula (IX)

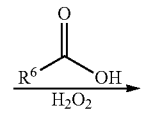

Formula (X)

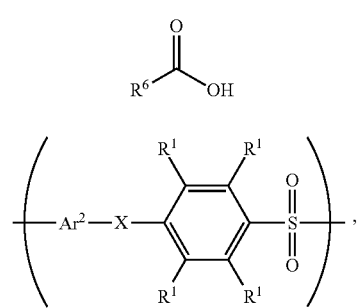

wherein X can be —O— or —NH—; R⁶ is C₁₋₆ alkyl group; and Ar² and R¹ have the same definition as above. The synthesis pathway of the above method for preparing the polymer having the repeat unit represented by Formula (X) is as follows:

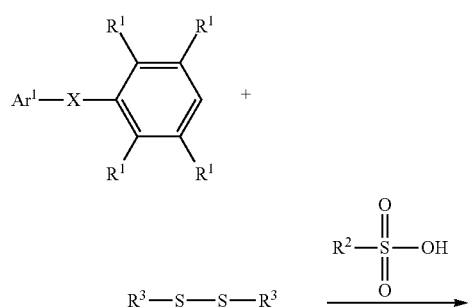

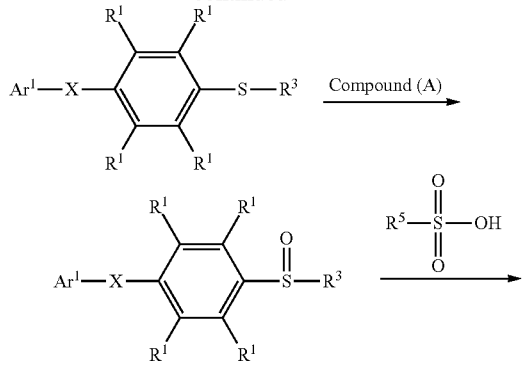

polymer having a repeat unit represented by Formula (VII)

nucleophile polymer having a repeat unit represented by Formula (VIII)

polymer having a repeat unit represented by Formula (X)

Formula (VII)

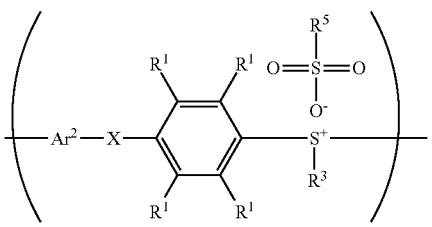

Formula (VIII)

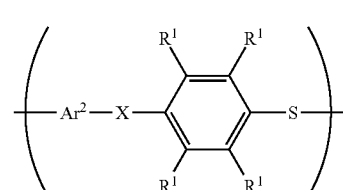

Formula (X)

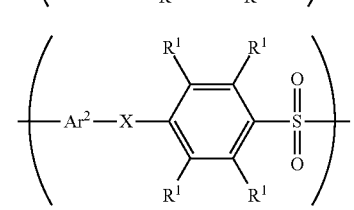

wherein X can be —O— or —NH—; and Ar¹, Ar², R¹, R², R³, R⁵ and R⁶ have the same definition as above.

According to other embodiments of the disclosure, in the method for preparing the polymer having the repeat unit represented by Formula (X) of the disclosure, the polymer having the repeat unit represented by Formula (VIII), the compound having the structure of Formula (IX), and hydrogen peroxide can be dissolved into a solvent before undergoing the reaction. For example, the solvent can be amide-type solvent or sulfoxide-type solvent.

According to embodiments of the disclosure, $R^6$ can be independently methyl group, ethyl group, propyl group, isopropyl group, n-butyl group, t-butyl group, sec-butyl group, isobutyl group, pentyl group, or hexyl group.

According to embodiments of the disclosure, when X of the repeat unit represented by Formula (VII) is —S— (i.e. the repeat unit represented by Formula (VII) is

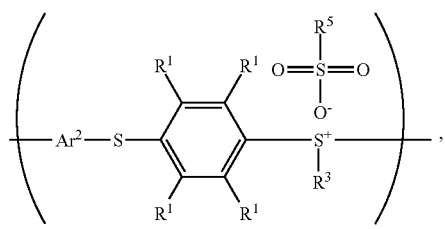

wherein $Ar^2$, $R^1$, $R^3$, and $R^5$ have the same definition as above), the method for preparing the polymer of the disclosure, after obtaining the polymer having the repeat unit represented by Formula (VII), can further include reacting the polymer having the repeat unit represented by Formula (VII) with hydrogen peroxide, obtaining a polymer having a repeat unit represented by Formula (XI). Alternatively, the polymer having the repeat unit represented by Formula (VII) is reacted with hydrogen peroxide in the presence of the compound having the structure of Formula (IX), obtaining the polymer having the repeat unit represented by Formula (XI).

Formula (VII)

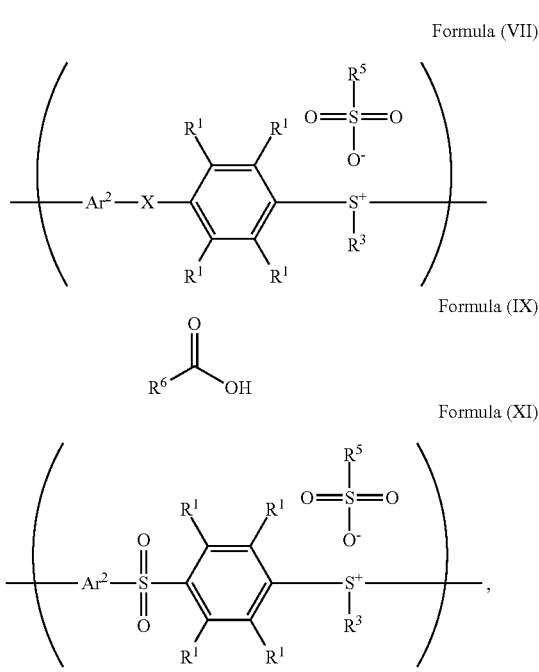

Formula (IX)

Formula (XI)

wherein X can be —S—; and $Ar^2$, $R^1$, $R^3$, $R^5$ and $R^6$ have the same definition as above. The synthesis pathway of the above method for preparing the polymer having the repeat unit represented by Formula (XI) is as follows:

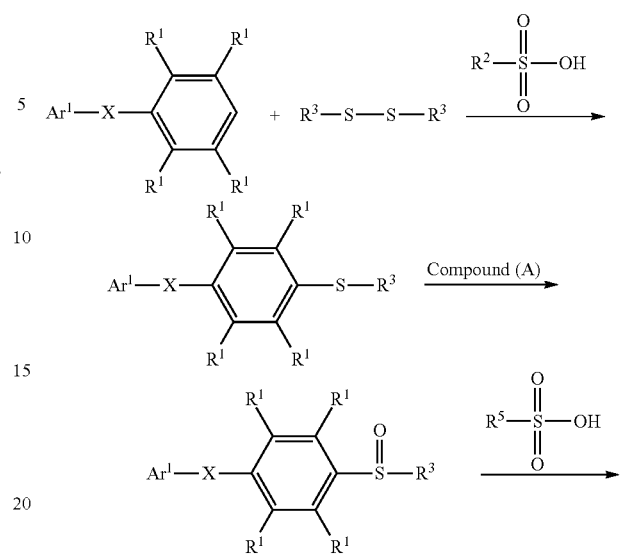

polymer having a repeat unit represented by Formula (VII)

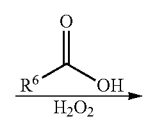

polymer having a repeat unit represented by Formula (XI)

Formula (VII)

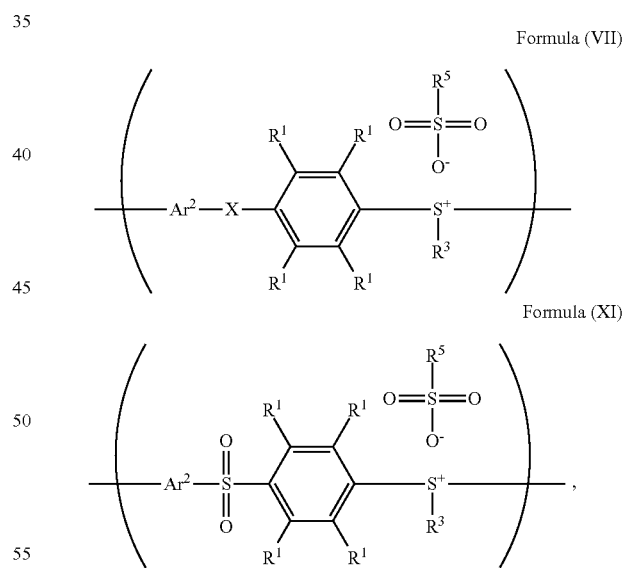

Formula (XI)

wherein X can be —S—; and $Ar^1$, $Ar^2$, $R^1$, $R^2$, $R^3$, $R^5$ and $R^6$ have the same definition as above.

According to other embodiments of the disclosure, in the method for preparing the polymer having a repeat unit represented by Formula (XI) of the disclosure, the polymer having the repeat unit represented by Formula (VII) and hydrogen peroxide can be dissolved into an organic solvent and then the mixture is reacted with the compound having the structure represented by Formula (IX) to undergo the reaction. For example, the solvent can be nitrile-type solvent, amide-type solvent, or sulfoxide-type solvent. Furthermore, the polymer having the repeat unit represented by Formula (VII), the compound having the structure represented by Formula (IX), and hydrogen peroxide can be dissolved into an organic solvent before undergoing the reaction.

According to embodiments of the disclosure, after preparing the polymer having a repeat unit represented by Formula (XI), the method for preparing the polymer of the disclosure can further include reacting a nucleophile with the polymer having the repeat unit represented by Formula (XI), obtaining a polymer having a repeat unit represented by Formula (XII)

polymer having a repeat unit represented by Formula (VII)

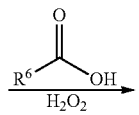

polymer having a repeat unit represented by Formula (XI)

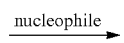

polymer having a repeat unit represented by Formula (XII)

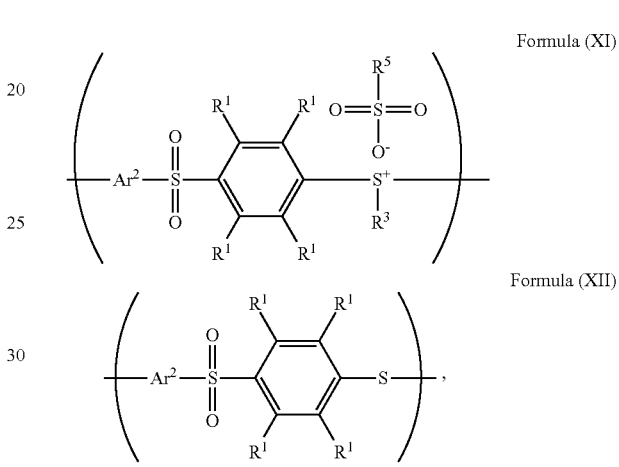

wherein X is —S—; and $Ar^1$, $Ar^2$, $R^1$, $R^2$, $R^3$, $R^5$, and $R^6$ have the same definition as above.

According to embodiments of the disclosure, the nucleophile can be substituted or unsubstituted pyridine or derivatives thereof (such as pyridine or 4-methylpyridine), amine (such as triethylamine), halogenated salt (such as potassium chloride), alcohol (such as methanol or ethanol), amide (such as dimethylformamide, dimethylacetamide, or N-methylpyrrolidone), or a combination thereof. The equivalent ratio of the nucleophile to the moiety represented by

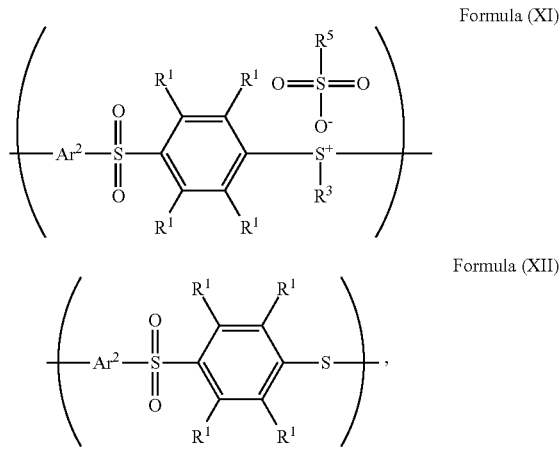

wherein $Ar^2$, $R^1$, $R^3$, and $R^5$ have the same definition as above. The synthesis pathway of the above method for preparing the polymer having the repeat unit represented by Formula (XII) is as follows:

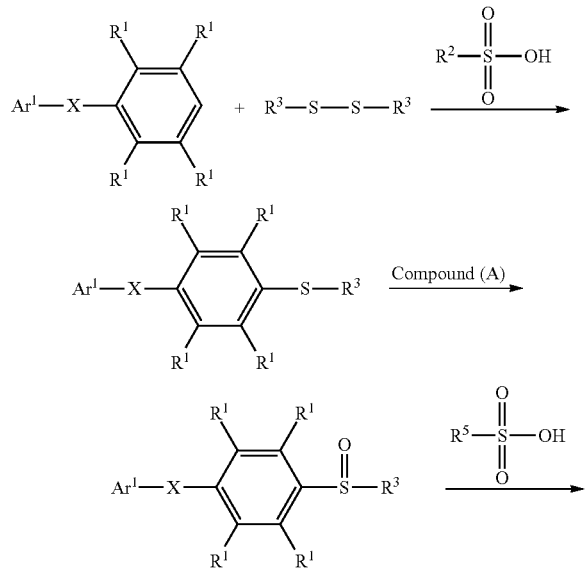

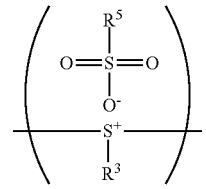

of the polymer having the repeat unit represented by Formula (XI) can be from 1 to 10. According to embodiments of the disclosure, the nucleophile and the polymer having the repeat unit represented by Formula (XI) can optionally be dissolved into an organic solvent before undergoing the reaction.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity.

Example 1

5 g of diphenyl ether, 11.7 g of benzenesulfonic acid, and 50 ml of dichloromethane were added into a reaction bottle under nitrogen atmosphere, and then cooled to 15° C. Next, 5.54 g of 1,2-dimethyldisulfane was added into the reaction bottle. After reacting at 15° C. for 20 hr, the result was mixed with 50 ml of sodium hydroxide aqueous solution (the weight ratio of sodium hydroxide to water is 1:10). After stirring for 0.5 hr, the result was extracted three times using dichloromethane and water as the extraction solvent. Next, an organic phase was separated and dried, obtaining Compound (1). The synthesis pathway of the above reaction was as follows:

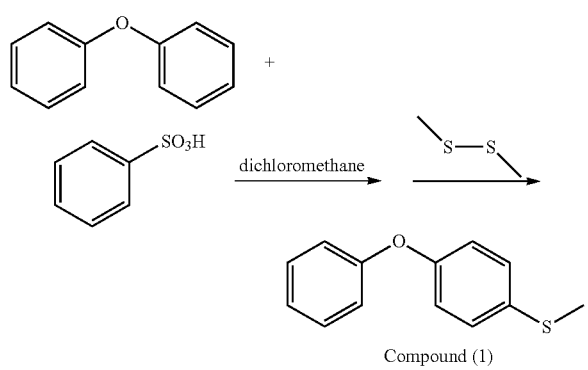

Compound (1)

Compound (1) was analyzed by nuclear magnetic resonance (NMR) spectroscopy and the result is as follows: $^1$H NMR (400 MHz, ppm, CDCl$_3$): 2.50 (—CH$_3$, 3H, s), 7.00 (phenyl, 4H, m), 7.14 (phenyl, 1H, t), 7.32-7.41 (phenyl, 4H, m).

Example 2

0.73 g of Compound (1), 12 ml of nitric acid aqueous solution (with a concentration of 20%), and 4 ml of acetonitrile were added into a reaction bottle. After stirring at room temperature for 4 hr, 10 ml of sodium hydroxide aqueous solution (with a concentration of 3%) was added into the reaction bottle. Next, after the reaction was complete, the result was separated and dried, obtaining Compound (2) (orange powder). The synthesis pathway of the above reaction was as follows:

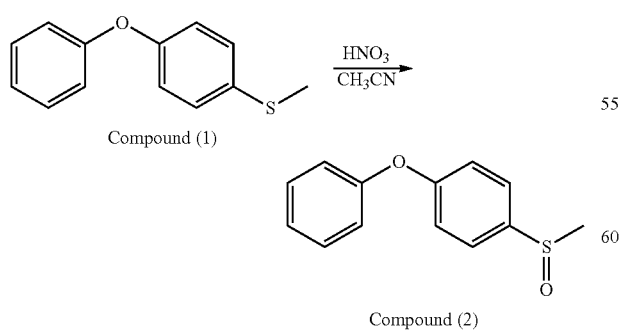

Compound (2) was analyzed by nuclear magnetic resonance (NMR) spectroscopy and the result is as follows: $^1$H NMR (400 MHz, ppm, CD$_3$CO): 2.71 (—CH$_3$, 3H, s), 7.10-7.25 (phenyl, 5H, m), 7.44-7.48 (phenyl, 2H, t), 7.70-7.72 (phenyl, 2H, d).

Example 3

0.65 g of Compound (2) was added into a reaction bottle. Next, 3 ml of methanesulfonic acid (CH$_3$SO$_3$H) was added into the reaction bottle placed in an ice bath. After reacting for 1 hr, the reaction bottle was raised to room temperature and then reacted at room temperature for 20 hr, obtaining a solution including Polymer (1). Next, the solution including Polymer (1) was added into 100 ml of ethyl ether and stirred for 30 min. Next, 6 ml of 4-methylpyridine was added under nitrogen atmosphere and then the result was stirred at 100° C. for 4-6 hr. After the reaction was complete, the result was added into 100 ml of hydrochloric acid solution (with a concentration of 10%) and then stirred for 10 min. After concentrating, Polymer (2) was obtained. The synthesis pathway of the above reaction was as follows:

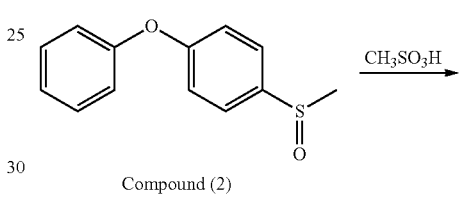

Compound (2)

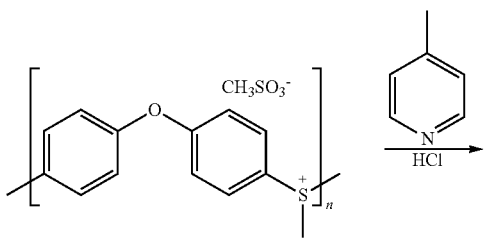

Polymer (1)

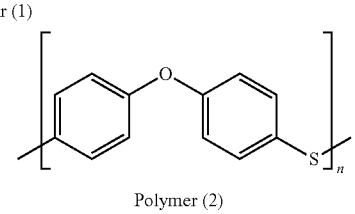

Polymer (2)

(n > 1)

Polymer (2) was analyzed by nuclear magnetic resonance (NMR) spectroscopy and the result is as follows: $^1$H NMR (400 MHz, ppm, (CD$_3$)$_2$SO): 7.04 (phenyl, d), 7.36 (phenyl, d).

Example 4

0.2 g of Polymer (2), 10 ml of acetic acid, 0.9 g of hydrogen peroxide solution (with a concentration of 30%) and 2 ml of dimethylacetamide (DMAc) were added into a reaction bottle, and the reaction bottle was stirred at 80° C. for 6 hr. Next, the result was concentrated, obtaining Polymer (3). The synthesis pathway of the above reaction was as follows:

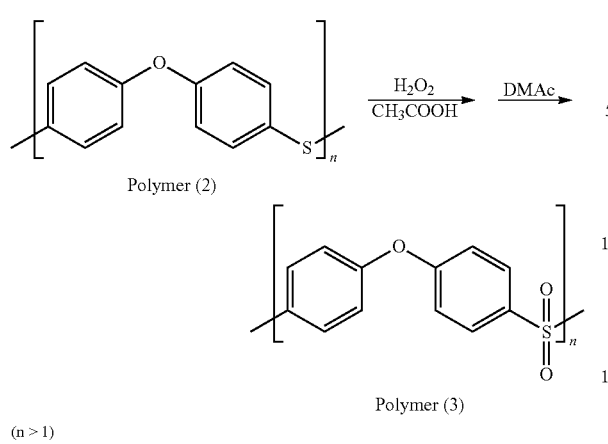

Polymer (2)

Polymer (3)

(n > 1)

Polymer (3) was analyzed by nuclear magnetic resonance (NMR) spectroscopy and the result is as follows: $^1$H NMR (400 MHz, ppm, $(CD_3)_2SO$): 7.28 (phenyl, d), 7.99 (phenyl, d). Next, Polymer (3) was analyzed by Fourier-transform infrared (FT-IR) spectroscopy, and the result shows that the strong absorption peaks are 1483 cm$^{-1}$ (characteristic vibration frequency of benzene ring), 1575 cm$^{-1}$ (characteristic vibration frequency of benzene ring), 1295 cm$^{-1}$ (asymmetry vibration frequency of S=O), 1318 cm$^{-1}$ (asymmetry vibration frequency of S=O), and 1145 cm$^{-1}$ (symmetry vibration frequency of S=O). The properties of Polymer (3) were measured by a differential scanning calorimetry (DSC), and the result shows Polymer (3) has a glass transition temperature (Tg) of about 210° C. Polymer (3) was analyzed by gel permeation chromatography (GPC), and the results show Polymer (3) has a weight average molecular weight (Mw) of about 128,287, a number average molecular weight (Mn) of about 85,435, and a polydispersity index (PDI) of about 1.5.

Example 5

5.58 g of diphenyl sulfide and 5.64 g of 1,2-dimethyldisulfane were added into a reaction bottle, and then 50 ml of dichloromethane as solvent was added into the reaction bottle. Next, 11.7 g of benzenesulfonic acid was added into the reaction bottle. After reacting at 15° C. for 44 hr, the result was extracted three times using 150 ml of n-hexane dichloromethane and water as the extraction solvent. Next, an organic phase was separated, dried, and purified by column chromatography, obtaining Compound (3). The synthesis pathway of the above reaction was as follows:

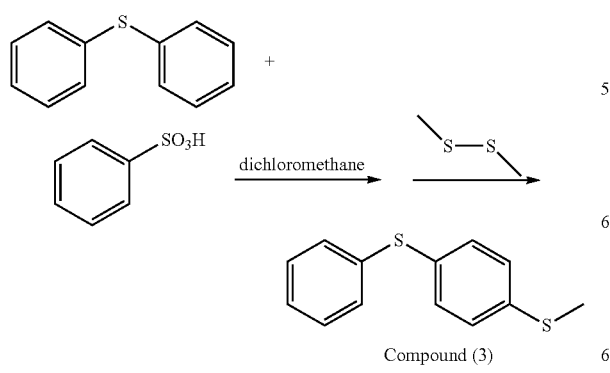

Compound (3) was analyzed by nuclear magnetic resonance (NMR) spectroscopy and the result is as follows: $^1$H NMR (400 MHz, ppm, CDCl$_3$): 2.50 (—CH$_3$, 3H, s), 7.21-7.34 (phenyl, 9H, m).

Example 6

5.07 g of Compound (3) was added into a reaction bottle, and then 20 ml of acetonitrile as solvent was added into the reaction bottle. Next, 60 ml of nitric acid aqueous solution (with a concentration of 20%) was added into the reaction bottle. After reacting at room temperature for 4 hr, 12 g of sodium hydroxide was added into the reaction bottle to neutralize the solution. The result was extracted three times using 150 ml of dichloromethane as the extraction solvent. Next, an organic phase was separated and dried, obtaining Compound (4). The synthesis pathway of the above reaction was as follows:

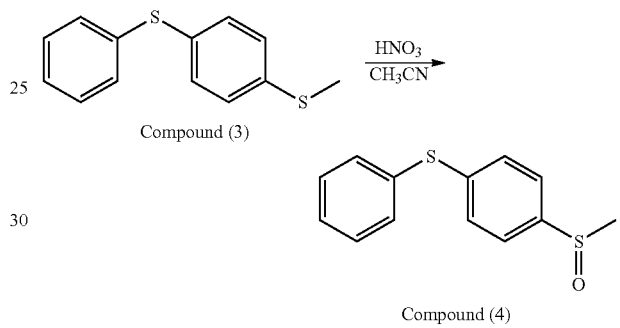

Compound (4) was analyzed by nuclear magnetic resonance (NMR) spectroscopy and the result is as follows: $^1$H NMR (400 MHz, ppm, CDCl$_3$): 2.73 (—CH$_3$, 3H, s), 7.34-7.49 (phenyl, 9H, m).

Example 7

3 g of Compound (4) was added into a reaction bottle, and 10 ml of methanesulfonic acid was added into the reaction bottle at 15° C. After reacting for 20 hr, 50 ml of water was added into the reaction bottle to cause a precipitation. The precipitate was separated and dried, obtaining a white solid. The white solid was dissolved in a solvent including 46 ml of chloroform and 46 ml of trifluoroacetic acid. Next, 4.14 g of hydrogen peroxide aqueous solution (with a concentration of 30%) was added and then the result was reacted at 60° C. for 5 hr. After the reaction was complete, the result was mixed with a water to cause a precipitation. The precipitate was separated and dried, obtaining Polymer (4). The synthesis pathway of the above reaction was as follows:

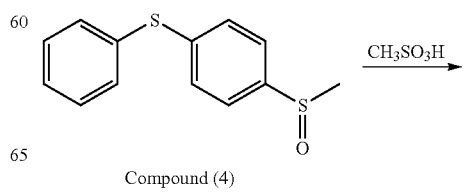

Compound (4)

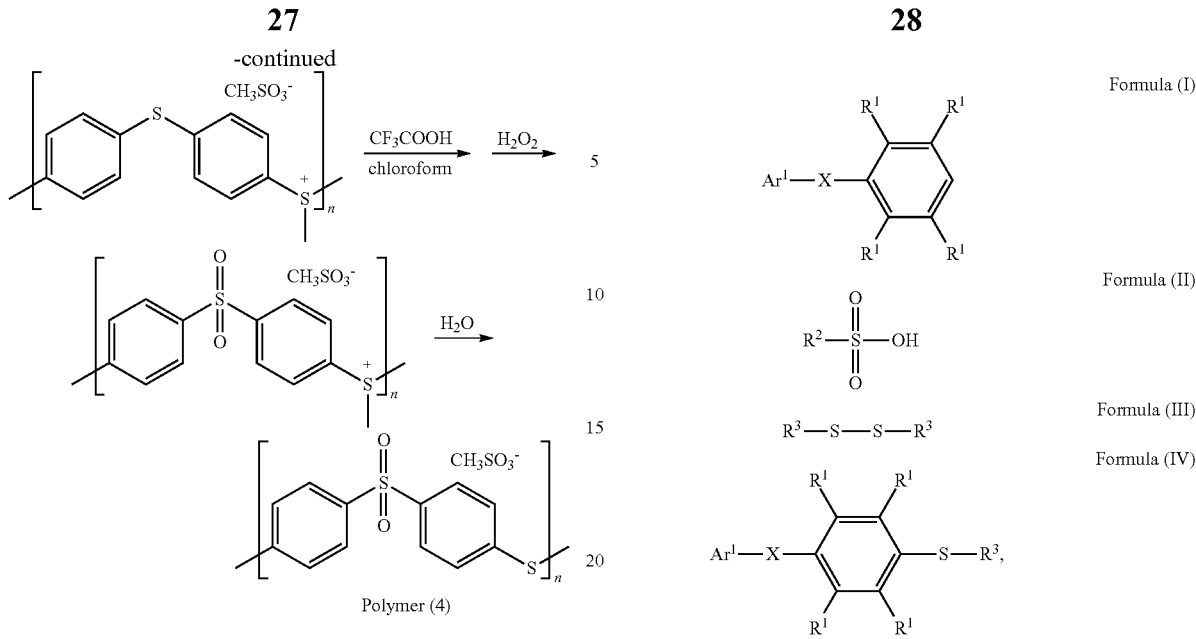

Polymer (4) was analyzed by nuclear magnetic resonance (NMR) spectroscopy and the result is as follows: $^1$H NMR (400 MHz, ppm, d$^6$-DMSO): 7.56 (phenyl, 4H, s), 7.93 (phenyl, 4H, s). The properties of Polymer (4) were measured by a differential scanning calorimetry (DSC), and the result shows Polymer (4) has a glass transition temperature (Tg) of about 222° C.

Accordingly, the disclosure provides a method for preparing a compound, wherein the starting material or catalyst of the method for preparing a compound is a halogen-free compound. Thus, no halogen-containing side product is formed. In addition, there is no halogen-containing compound remained in the obtained result. The method for preparing a compound of the disclosure does not include an additional step for removing a halogen-containing side product or residual halogen-containing compound, thereby reducing preparation cost and increasing product yield. Thus, a halogen-free monomer, which can be used in a subsequent polymerization, is obtained. Furthermore, the disclosure also provides a method for preparing a polymer (such as polyether sulfone (PES) or polythioether sulfone (PTES)). Since the method for preparing a polymer includes subjecting a monomer to an electrophilic polymerization in an acidic environment and then performing an oxidation after polymerization, the obtained polymer exhibits increased molecular weight and relatively low polydispersity index (PDI).

It will be clear that various modifications and variations can be made to the disclosed methods and materials. It is intended that the specification and examples be considered as exemplary only, with the true scope of the disclosure being indicated by the following claims and their equivalents.

What is claimed is:

1. A method for preparing a compound, comprising:
reacting a compound having a structure represented by Formula (I) with a compound having a structure represented by Formula (III) in the presence of a compound having a structure represented by Formula (II), obtaining a compound having a structure represented by Formula (IV)

wherein Ar$^1$ is substituted or unsubstituted aryl group; X is —O—, —S—, or —NH—; R$^1$ is independently hydrogen or C$_{1-6}$ alkyl group; R$^2$ is hydroxyl group, C$_{1-6}$ alkyl group, phenyl group, or tolyl group; and R$^3$ is independently C$_{1-6}$ alkyl group, C$_{5-8}$ cycloalkyl group, or C$_{2-6}$ alkoxyalkyl group.

2. The method as claimed in claim 1, wherein Ar$^1$ is substituted or unsubstituted phenyl group, biphenyl group, naphthyl group, thienyl group, indolyl group, phenanthrenyl group, indenyl group, anthracenyl group, or fluorenylene group.

3. The method as claimed in claim 1, wherein R$^1$ is independently hydrogen, methyl group, ethyl group, propyl group, isopropyl group, n-butyl group, t-butyl group, sec-butyl group, isobutyl group, pentyl group, or hexyl group.

4. The method as claimed in claim 1, wherein the compound having the structure of Formula (I) is

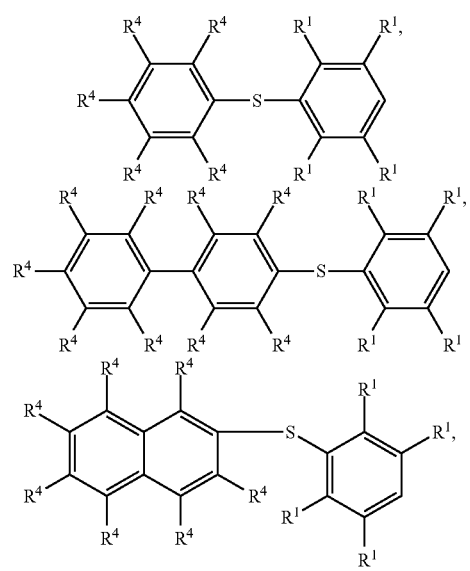

-continued

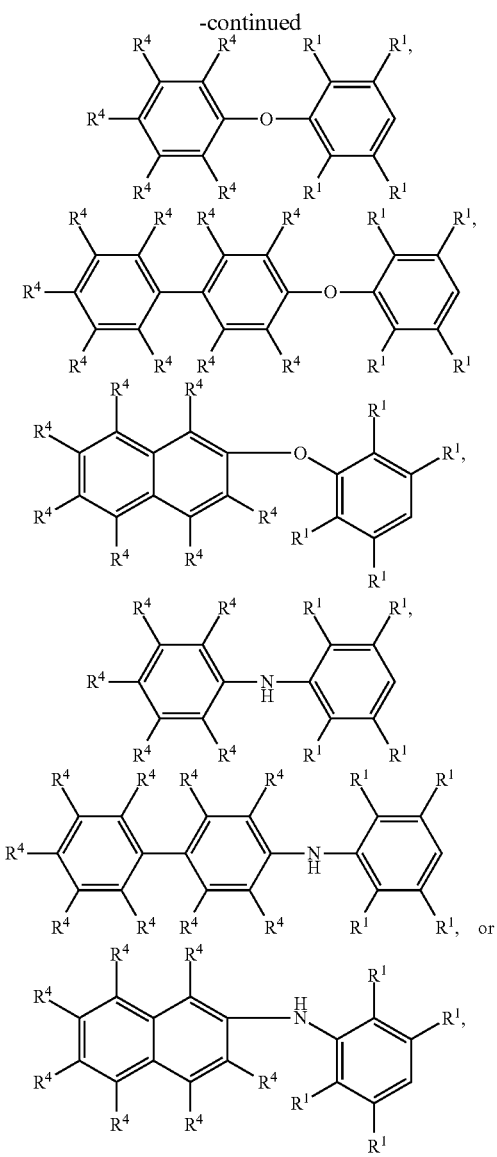

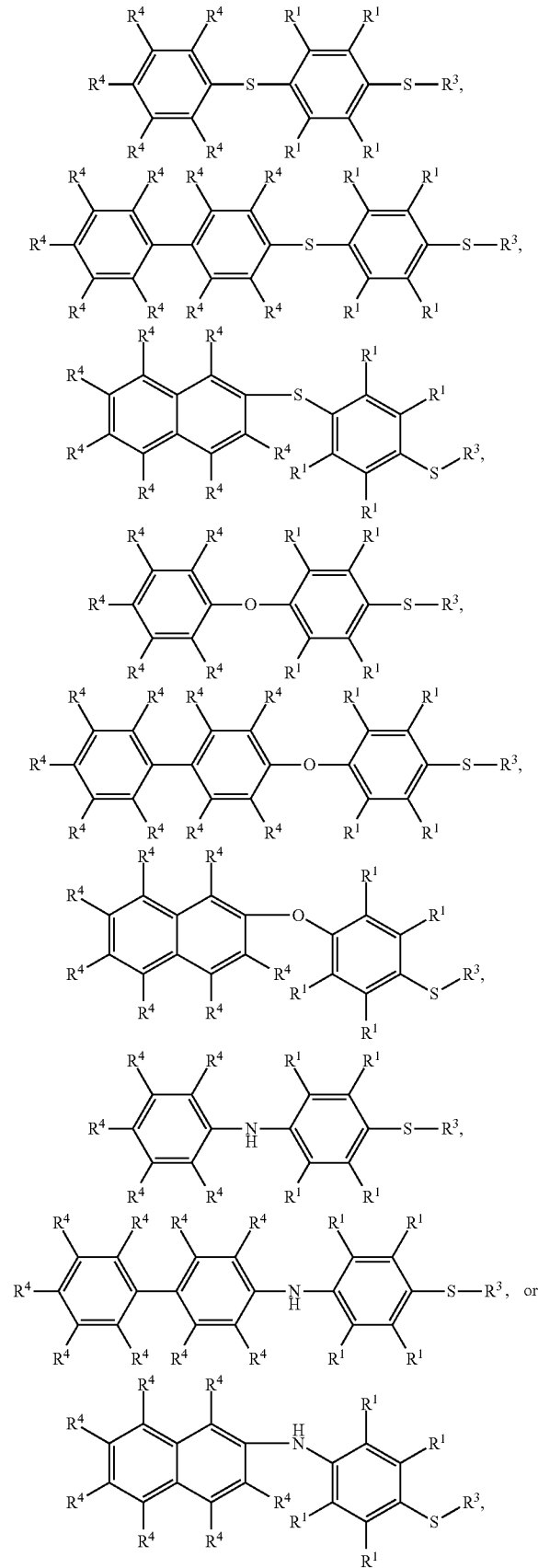

wherein R¹ is independently hydrogen or $C_{1-6}$ alkyl group; and R⁴ is independently hydrogen or $C_{1-6}$ alkyl group.

5. The method as claimed in claim 1, wherein the compound having the structure of Formula (II) is sulfuric acid, methanesulfonic acid, benzenesulfonic acid, p-toluenesulfonic acid, or a combination thereof.

6. The method f as claimed in claim 1, wherein R³ is independently methyl group, ethyl group, propyl group, isopropyl group, n-butyl group, t-butyl group, sec-butyl group, isobutyl group, pentyl group, hexyl group, cyclopentyl group, cyclohexyl group, cycloheptyl group, cyclooctyl group, or

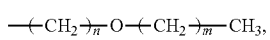

wherein $1 \leq n \leq 5$, $0 \leq m \leq 4$, and $1 \leq n+m \leq 5$.

7. The method as claimed in claim 1, wherein the compound having the structure of Formula (IV) is wherein R¹ is independently hydrogen or C$_{1-6}$ alkyl group; R⁴ is independently hydrogen or C$_{1-6}$ alkyl group; and R³ is independently C$_{1-6}$ alkyl group, C$_{5-8}$ cycloalkyl group, or C$_{2-6}$ alkoxyalkyl group.

8. The method as claimed in claim 1, further comprising:

reacting the compound having the structure represented by Formula (IV) with a compound (A), obtaining a compound having the structure represented by Formula (V)

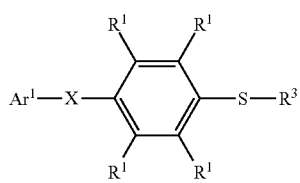

Formula (IV)

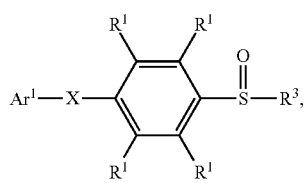

Formula (V)

wherein the compound (A) is nitric acid, sulfuric acid, acetic acid, hydrogen peroxide, or a combination thereof; Ar¹ is substituted or unsubstituted; X is —O—, —S—, or —NH—; R¹ is independently hydrogen or C$_{1-6}$ alkyl group; and R³ is independently C$_{1-6}$ alkyl group, C$_{5-8}$ cycloalkyl group, or C$_{2-6}$ alkoxyalkyl group.

9. The method as claimed in claim 8, wherein the compound having the structure of Formula (V) is

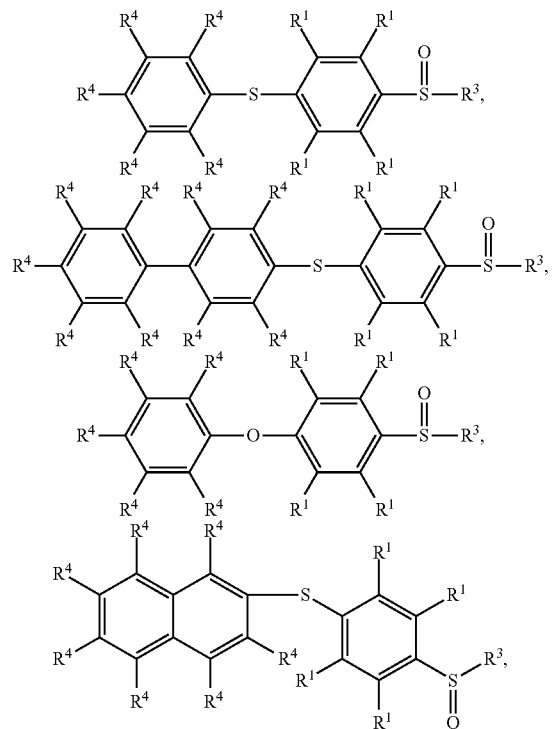

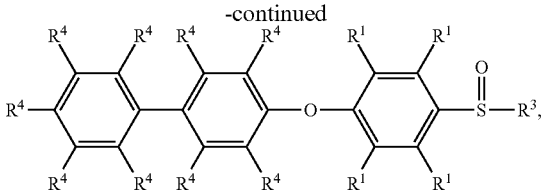

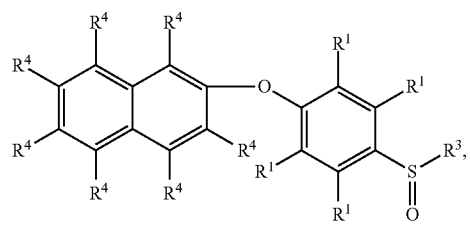

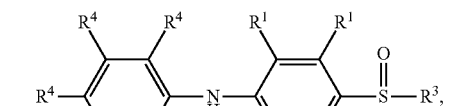

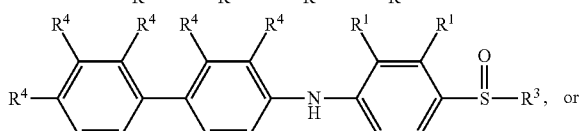

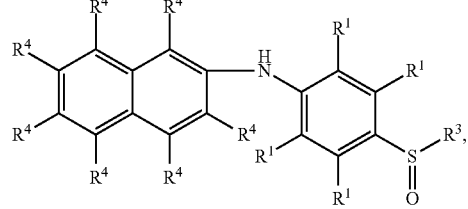

wherein R¹ is independently hydrogen or C$_{1-6}$ alkyl group; R⁴ is independently hydrogen or C$_{1-6}$ alkyl group; and R³ is independently C$_{1-6}$ alkyl group, C$_{5-8}$ cycloalkyl group, or C$_{2-6}$ alkoxyalkyl group.

10. A method for preparing a polymer, comprising:

reacting a compound having a structure represented by Formula (I) with a compound having a structure represented by Formula (III) in the presence of a compound having a structure represented by Formula (II), obtaining a compound having a structure represented by Formula (IV);

reacting the compound having the structure represented by Formula (IV) with a compound (A), obtaining a compound having the structure represented by Formula (V), wherein the compound (A) is nitric acid, sulfuric acid, acetic acid, hydrogen peroxide, or a combination thereof; and reacting the compound having the structure represented by Formula (V) with a compound having a structure represented by Formula (VI), obtaining a polymer having a repeat unit represented by Formula (VII)

Formula (I)

Ar¹—X—[phenyl with R¹ substituents]

Formula (II)

$R^2-\overset{O}{\underset{O}{S}}-OH$

Formula (III)

$R^3-S-S-R^3$

Formula (IV)

Ar¹—X—[phenyl with R¹ substituents]—S—R³

Formula (V)

Ar¹—X—[phenyl with R¹ substituents]—S(=O)—R³

Formula (VI)

$R^5-\overset{O}{\underset{O}{S}}-OH$

Formula (VII)

$\left(-Ar^2-X-[\text{phenyl with } R^1]-\overset{R^5}{\underset{R^3}{S^+}}(O=S=O-O^-)\right)$

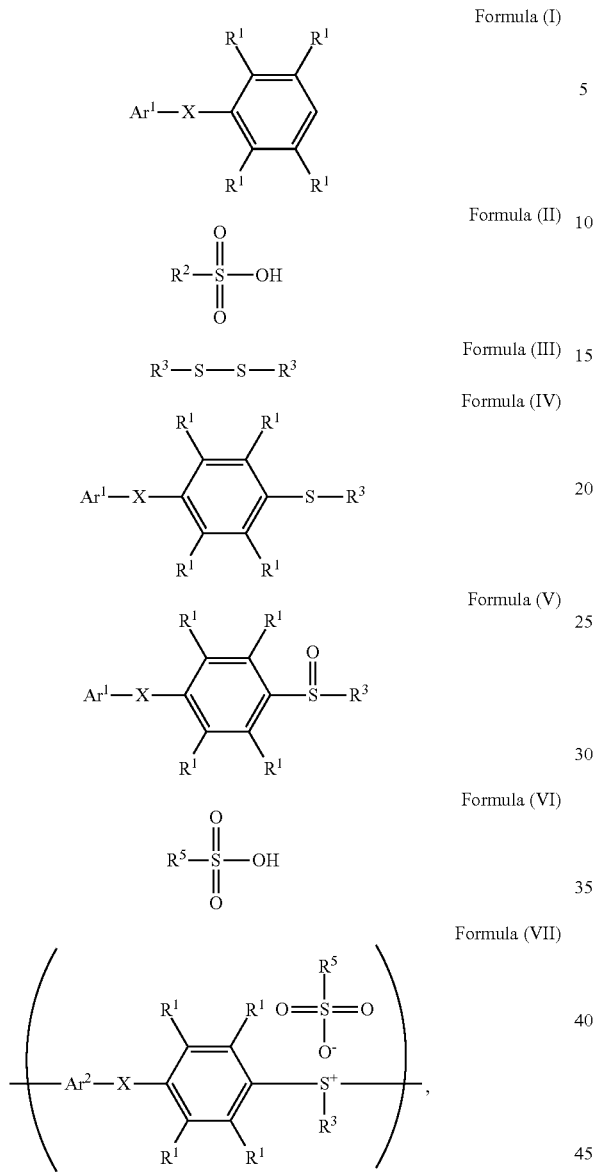

wherein Ar¹ is substituted or unsubstituted aryl group; X is —O—, —S—, or —NH—; R¹ is independently hydrogen or $C_{1-6}$ alkyl group; R² is hydroxyl group, $C_{1-6}$ alkyl group, phenyl group, or tolyl group; R³ is independently $C_{1-6}$ alkyl group, $C_{5-8}$ cycloalkyl group, or $C_{2-6}$ alkoxyalkyl group; R⁵ is hydroxyl group, $C_{1-6}$ alkyl group, phenyl group, or tolyl group; and Ar² is substituted or unsubstituted aryl diradical.

11. The method as claimed in claim 10, wherein Ar¹ is substituted or unsubstituted phenyl group, biphenyl group, naphthyl group, thienyl group, indolyl group, phenanthrenyl group, indenyl group, anthracenyl group, or fluorenylene group.

12. The method as claimed in claim 10, wherein R¹ is independently hydrogen, methyl group, ethyl group, propyl group, isopropyl group, n-butyl group, t-butyl group, sec-butyl group, isobutyl group, pentyl group, or hexyl group.

13. The method as claimed in claim 10, wherein the compound having the structure of Formula (I) is wherein $R^1$ is independently hydrogen or $C_{1-6}$ alkyl group; and $R^4$ is independently hydrogen or $C_{1-6}$ alkyl group.

14. The method as claimed in claim 10, wherein the compound having the structure of Formula (II) is sulfuric acid, methanesulfonic acid, benzenesulfonic acid, p-toluenesulfonic acid or a combination thereof.

15. The method as claimed in claim 10, wherein $R^3$ is independently methyl group, ethyl group, propyl group, isopropyl group, n-butyl group, t-butyl group, sec-butyl group, isobutyl group, pentyl group, hexyl group, cyclopentyl group, cyclohexyl group, cycloheptyl group, cyclooctyl group, or

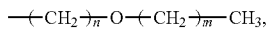

wherein $1 \leq n \leq 5$, $0 \leq m \leq 4$, and $1 \leq n+m \leq 5$.

16. The method as claimed in claim 10, wherein the compound having the structure of Formula (IV) is

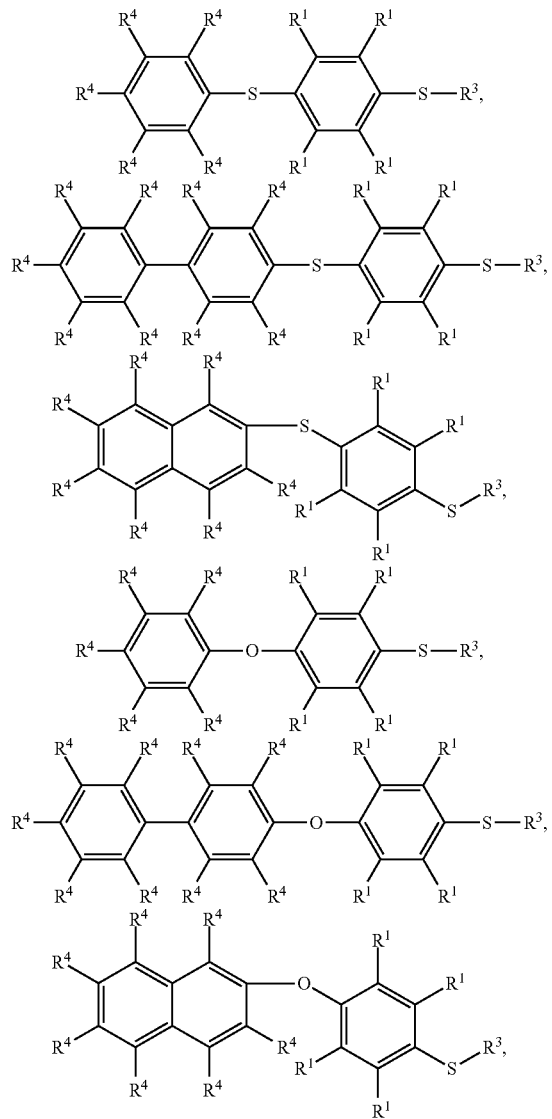

wherein $R^1$ is independently hydrogen or $C_{1-6}$ alkyl group; $R^4$ is independently hydrogen or $C_{1-6}$ alkyl group; and $R^3$ is independently $C_{1-6}$ alkyl group, $C_{5-8}$ cycloalkyl group, or $C_{2-6}$ alkoxyalkyl group.

17. The method as claimed in claim 10, wherein the compound having the structure of Formula (V) is

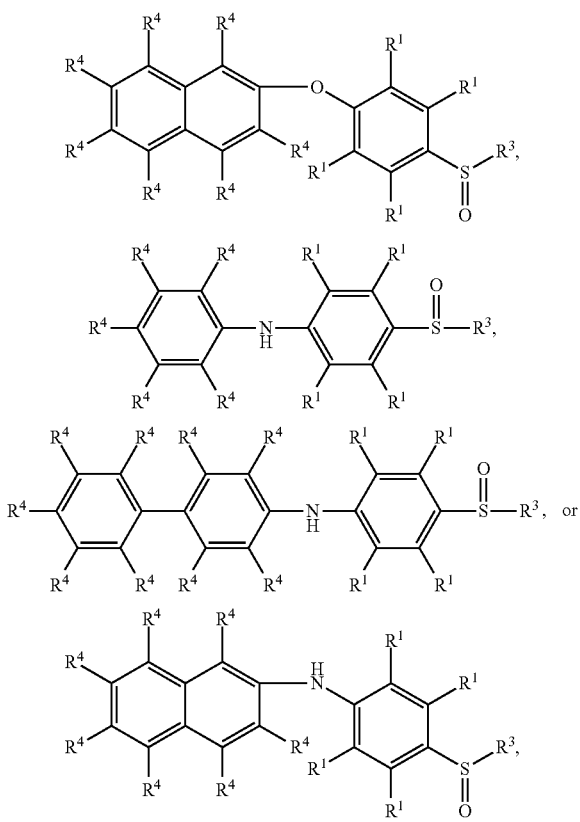

wherein R¹ is independently hydrogen or $C_{1-6}$ alkyl group; R⁴ is independently hydrogen or $C_{1-6}$ alkyl group; and R³ is independently $C_{1-6}$ alkyl group, $C_{5-8}$ cycloalkyl group, or $C_{2-6}$ alkoxyalkyl group.

18. The method as claimed in claim 10, wherein the compound having the structure of Formula (VI) is sulfuric acid, methanesulfonic acid, benzenesulfonic acid, p-toluenesulfonic acid, or a combination thereof.

19. The method as claimed in claim 10, wherein Ar² is substituted or unsubstituted phenylene group, biphenylene group, naphthylene group, thienylene group, indolylene group, phenanthrenylene group, indenylene group, anthracenylene group, or fluorenylene group.

20. The method as claimed in claim 10, further comprising:

reacting a nucleophile with the polymer having the repeat unit represented by Formula (VII), obtaining a polymer having a repeat unit represented by Formula (VIII)

Formula (VII)

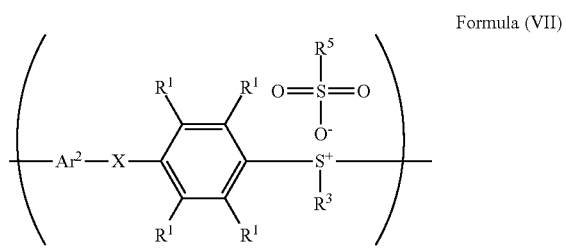

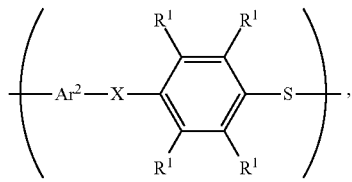
Formula (VIII)

wherein X is —O—, —S—, or —NH—; R¹ is independently hydrogen or $C_{1-6}$ alkyl group; R³ is independently $C_{1-6}$ alkyl group, $C_{5-8}$ cycloalkyl group, or $C_{2-6}$ alkoxyalkyl group; R⁵ is hydroxyl group, $C_{1-6}$ alkyl group, phenyl group, or tolyl group; and Ar² is substituted or unsubstituted aryl diradical.

21. The method as claimed in claim 20, wherein the nucleophile is pyridine, 4-methylpyridine, triethylamine, potassium chloride, methanol, ethanol, dimethylformamide, dimethylacetamide, N-methylpyrrolidone, or a combination thereof.

22. The method as claimed in claim 20, when X of the polymer having the repeat unit represented by Formula (VIII) is —O— or —NH—, further comprising:

reacting the polymer having the repeat unit represented by Formula (VIII) with hydrogen peroxide, obtaining a polymer having a repeat unit represented by Formula (X)

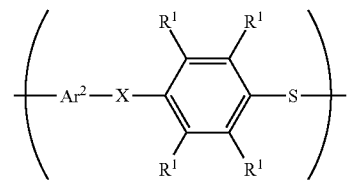
Formula (VIII)

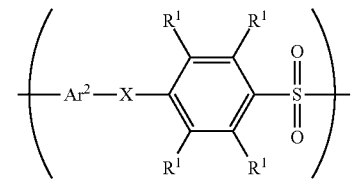
Formula (X)

wherein X is —O— or —NH—; R¹ is independently hydrogen or $C_{1-6}$ alkyl group; and Ar² is substituted or unsubstituted aryl diradical.

23. The method as claimed in claim 20, wherein a polymer having the repeat unit represented by Formula (VIII) is reacted with hydrogen peroxide in the presence of a compound having a structure represented by Formula (IX)

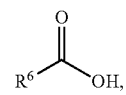
Formula (IX)

wherein R⁶ is $C_{1-6}$ alkyl group.

24. The method as claimed in claim 10, when X of the polymer having the repeat unit represented by Formula (VII) is —S—, further comprising:

reacting the polymer having the repeat unit represented by Formula (VII) with hydrogen peroxide, obtaining a polymer having a repeat unit represented by Formula (XI)

Formula (VII)

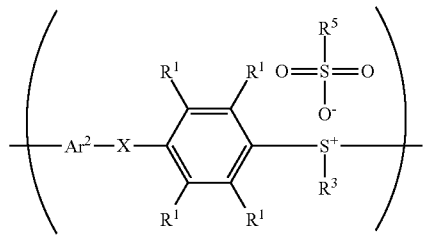

Formula (XI)

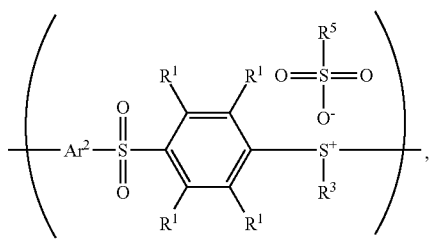

wherein X is —S—; $R^1$ is independently hydrogen or $C_{1-6}$ alkyl group; $R^3$ is independently $C_{1-6}$ alkyl group, $C_{5-8}$ cycloalkyl group, or $C_{2-6}$ alkoxyalkyl group; $R^5$ is hydroxyl group, $C_{1-6}$ alkyl group, phenyl group, or tolyl group; and $Ar^2$ is substituted or unsubstituted aryl diradical.

25. The method as claimed in claim 24, wherein the polymer having the repeat unit represented by Formula (VII) is reacted with hydrogen peroxide in the presence of a compound having a structure represented by Formula (IX)

Formula (IX)

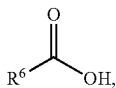

wherein $R^6$ is $C_{1-6}$ alkyl group.

26. The method as claimed in claim 24 further comprising:
reacting a nucleophile with the polymer having the repeat unit represented by Formula (XI), obtaining a polymer having a repeat unit represented by Formula (XII)

Formula (XI)

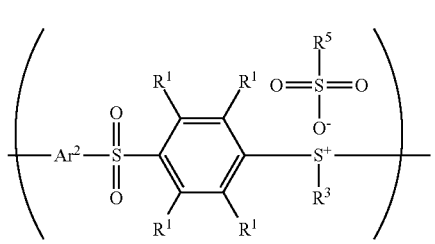

Formula (XII)

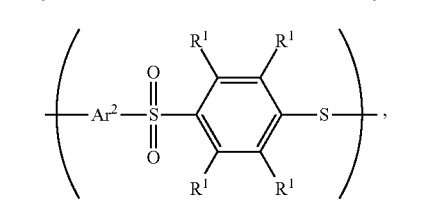

wherein $R^1$ is independently hydrogen or $C_{1-6}$ alkyl group; $R^3$ is independently $C_{1-6}$ alkyl group, $C_{5-8}$ cycloalkyl group, or $C_{2-6}$ alkoxyalkyl group; $R^5$ is hydroxyl group, $C_{1-6}$ alkyl group, phenyl group, or tolyl group; and $Ar^2$ is substituted or unsubstituted aryl diradical.

27. The method as claimed in claim 26, wherein the nucleophile is pyridine, 4-methylpyridine, triethylamine, potassium chloride, methanol, ethanol, dimethylformamide, dimethylacetamide, N-methylpyrrolidone, or a combination thereof.

* * * * *